United States Patent
Benedetti et al.

(10) Patent No.: US 7,517,881 B2
(45) Date of Patent: Apr. 14, 2009

(54) TRIAZINE DERIVATIVES, THEIR PREPARATION AND THERAPEUTIC APPLICATION THEREOF

(75) Inventors: Yannick Benedetti, Rosny Sous Bois (FR); Andrees Bohme, Paris (FR); Arielle Genevois-Borella, Thiais (FR); Gaetan Touyer, Chelles (FR); Jidong Zhang, Paris (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 11/869,260

(22) Filed: Oct. 9, 2007

(65) Prior Publication Data

US 2008/0096891 A1  Apr. 24, 2008

Related U.S. Application Data

(63) Continuation of application No. PCT/FR2006/000887, filed on Apr. 21, 2006.

(30) Foreign Application Priority Data

Apr. 22, 2005  (FR) .................................. 05 04042

(51) Int. Cl.
| | |
|---|---|
| C07D 253/065 | (2006.01) |
| C07D 403/04 | (2006.01) |
| A61K 31/53 | (2006.01) |
| A61P 19/02 | (2006.01) |
| A61P 25/18 | (2006.01) |
| A61P 25/04 | (2006.01) |

(52) U.S. Cl. ...................................... 514/242; 544/182
(58) Field of Classification Search ................ 544/182; 514/242
See application file for complete search history.

(56) References Cited

FOREIGN PATENT DOCUMENTS

JP  2002030084  1/2002

WO  WO 03/029252  4/2003

OTHER PUBLICATIONS

Arneric et al., Biochemical Pharmacology, 74, 1092-1101, 2007.*
Decker et al., Expert Opin. Investig. Drugs, 10(10), 18-19-1820, 2001.*
West, Solid State Chemistry and its Applications, Wiley, New York, 1988, pp. 358 & 365.*
Vippagunta et al., Advanced Drug Delivery Reviews 48: 3-26, 2001.*
Burch, H. A., et. al., Nitrofuryl Heterocycles, X. Analogs of 6-(5-Nitro-2-Furyl)-as-Triazine-3,5,(2H,4H)-Dione, Journal of Medicinal Chemistry, vol. 13, No. 2, pp. 288-291 (1970).
Lalezari, I., et. al., 1,2,4-Triazines VIII. The Synthesis of 1,2,4-Triazino [2,3-e] Pyrazolo [1,5-a]—1,3,5-Triazines and 1,2,4-Triazino [4,3-e} Pyrazolo [1,5-a]—1,3,5—Triazines, Journal of Heterocyclic Chemistry, vol. 13, No. 6, pp. 1249-1251, (1976).
Lavergne, J. P., et. al., Research in the Azabenzodiazepine Series. IV. 1-(3'-Triazinyl) Ethylenediamines, Synthetic Intermediates For 7,8,9,10-Tetrahydro-(2H)(6H)-as-Triazino[2,3-c]-1, 3,5,-Triazepines, Bulletin De La Societe Chimique De France, (11-12, PT.) pp. 1827-1828, (1976).
Reid, W., et. al., Nucleophile Reaktionen an Chlor-N-(2-oxoacyl)Formamidinen, Liebigs Annalanen Der Chemie, vol. 2, pp. 141-148 (1988).

* cited by examiner

*Primary Examiner*—Venkataraman Balasubramanian
(74) *Attorney, Agent, or Firm*—Balaram Gupta

(57) ABSTRACT

The invention relates to triazine derivatives of general formula (I):

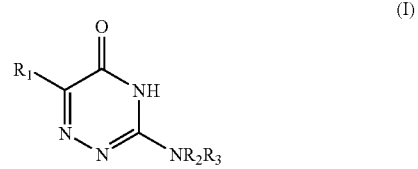

Wherein $R_1$, $R_2$ and $R_3$ are as defined herein. The invention also relates to a method for preparing these triazine derivatives and to the therapeutic application thereof.

25 Claims, No Drawings

TRIAZINE DERIVATIVES, THEIR PREPARATION AND THERAPEUTIC APPLICATION THEREOF

This application is a continuation of International application No. PCT/FR2006/000,887, filed Apr. 21, 2006, which is incorporated herein by reference in its entirety; which claims the benefit of priority of French Patent Application No. 05/04, 042, filed Apr. 22, 2005.

The invention relates to derivatives of triazines, their preparation and their application in therapeutics.

The compounds of the invention are novel ligands of acetylcholine receptors of the nicotinic type. These compounds are characterized more particularly in that they are ligands of type α7 nicotinic receptors.

The present invention relates to the compounds corresponding to formula (I)

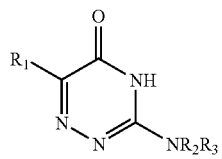

in which $R_1$ represents a heteroaryl or aryl group, said heteroaryl or aryl groups being optionally substituted by one or more groups selected from the halogen atoms and the $(C_1-C_4)$alkyl, $(C_1-C_4)$alkoxy, $(C_3-C_7)$cycloalkyl, aryl, hydroxy, cyano, $-NH_2$, $-NO_2$ groups;

$R_2$ represents a hydrogen atom or a $(C_1-C_4)$alkyl group;

$R_3$ represents
- a group $-(CH_2)n-NR_4R_5$ in which
  - n is equal to 2, 3 or 4 and
  - $R_4$ and $R_5$ represent, independently of one another, a $(C_1-C_4)$alkyl, or $(C_3-C_7)$cycloalkyl group, or alternatively $R_4$ and $R_5$ form together, with the nitrogen atom which carries them, a $(C_3-C_9)$heterocycloalkyl group; or
- a group $-(CH_2)mR_6$ in which
  - m is equal to 0, 1, 2, 3 or 4 and
  - $R_6$ represents a $(C_3-C_9)$heterocycloalkyl group having at least one nitrogen atom and bound to the triazine ring by a carbon atom, the $(C_3-C_9)$heterocycloalkyl group being optionally substituted by one or more $(C_1-C_4)$alkyl groups, or alternatively $R_2$ and $R_3$ form together, with the nitrogen atom which carries them, a $(C_5-C_9)$heterocycloalkyl containing 2 nitrogen atoms;

with the condition that, when $R_1$ represents a phenyl, $R_4$ and $R_5$ do not represent a methyl simultaneously.

The compounds of formula (I) can contain one or more asymmetric carbon atoms. They can therefore exist in the form of enantiomers or of diastereoisomers. These enantiomers, diastereoisomers, and mixtures thereof, including the racemic mixtures, form part of the invention.

The compounds of formula (I) can exist as bases or as salts of addition to acids. These salts of addition form part of the invention.

These salts can be prepared with pharmaceutically acceptable acids, but the salts of other acids that can be used, for example, for the purification or isolation of the compounds of formula (I) are also part of the invention.

The compounds of formula (I) can also exist in the form of hydrates or of solvates, namely in the form of associations or of combinations with one or more molecules of water or with a solvent. Said hydrates and solvates are also part of the invention.

The following definitions are used within the scope of the present invention:

- $(C_t-C_z)$ where t and z can take values from 1 to 9 represents a carbon chain that can have from 1 to 9 carbon atoms;
- a halogen atom: a fluorine, a chlorine, a bromine or an iodine;
- an alkyl group: a saturated, linear or branched aliphatic group. We may mention, as examples, the methyl, ethyl, propyl, isopropyl, butyl, isobutyl, tertbutyl, pentyl, etc. groups;
- an alkoxy group: a radical —O-alkyl where the alkyl group is as defined previously;
- a cycloalkyl group: a cyclic alkyl group. We may mention, as examples, the cyclopropyl, cyclobutyl, cyclopentyl, cyclohexyl, etc. groups;
- a heterocycloalkyl group: a saturated heterocycle containing from 1 to 2 heteroatoms, such as nitrogen, oxygen or sulfur, and being optionally bridged, i.e. optionally containing a carbon bond of 1 to 3 carbon atoms between 2 atoms of the ring. As examples of heterocycloalkyl groups, we may mention the pyrrolidinyl, piperidinyl, perhydro-azepinyl, perhydro-1,4-oxazepinyl, perhydro-1,4-thiazepinyl, perhydro-1,4-diazepinyl, 7-aza-bicyclo[2.2.1]heptanyl, 1-aza-bicyclo[2.2.1]heptanyl, 1-aza-bicyclo[2.2.2]octanyl, 2-aza-bicyclo[2.2.2]octanyl, 1-aza-bicyclo[3.2.1]octanyl, 8-aza-bicyclo[3.2.1]octanyl, 3-aza-bicyclo[3.2.1]octanyl, 1-aza-bicyclo[3.2.2]nonanyl, 3-aza-bicyclo[3.2.2]nonanyl, 1-aza-bicyclo[3.3.1]nonanyl, 3-aza-bicyclo[3.3.1]nonanyl, 9-aza-bicyclo[3.3.1]nonanyl, 1,4-diaza-bicyclo[3.2.2]nonanyl groups;
- an aryl group: a cyclic aromatic group containing from 6 to 10 carbon atoms. As examples of aryl groups, we may mention the phenyl, naphthyl, indenyl groups;
- a heteroaryl group: a cyclic aromatic group containing from 1 to 9 carbon atoms and containing from 1 to 3 heteroatoms, such as nitrogen, oxygen or sulfur. As examples of heteroaryl groups, we may mention the furanyl, thienyl, pyrrolyl, oxazolyl, thiazolyl, imidazolyl, pyrazolyl, isoxazolyl, isothiazolyl, isoxadiazolyl, isothiadiazolyl, oxadiazolyl, triazolyl, tetrazolyl, thiadiazolyl, pyridinyl, pyridazinyl, pyrimidinyl, pyrazinyl, triazinyl, indolyl, isoindolyl, benzofuranyl, benzothienyl, indazolyl, benzimidazolyl, benzothiazolyl, quinolinyl, isoquinolinyl, azaindolyl groups.

Among the compounds of formula (I) covered by the invention, a first subgroup of compounds comprises compounds for which:

$R_1$ represents a heteroaryl group, more particularly a furanyl, thienyl, pyrrolyl, oxazolyl, thiazolyl, imidazolyl, pyrazolyl, isoxazolyl, isothiazolyl, isoxadiazolyl, isothiadiazolyl, oxadiazolyl, triazolyl, tetrazolyl, thiadiazolyl, pyridinyl, pyridazinyl, pyrimidinyl, pyrazinyl, triazinyl, indolyl, isoindolyl, benzofuranyl, benzothienyl, indazolyl, benzimidazolyl, benzothiazolyl, quinolinyl, isoquinolinyl, azaindolyl, said heteroaryl group being optionally substituted by one or more groups, more particularly by one or two groups, selected from the halogen atoms and the $(C_1-C_4)$ alkyl, $(C_1-C_4)$alkoxy, $(C_3-C_7)$cycloalkyl, aryl, hydroxy, cyano, $-NH_2$, $-NO_2$ groups.

Among the compounds of formula (I) covered by the invention, a second subgroup of compounds comprises compounds for which:

$R_1$ represents a heteroaryl group, more particularly a furanyl, thienyl, pyrrolyl, pyrazolyl, triazolyl, imidazolyl, indolyl, indazolyl, benzothienyl, azaindolyl or aryl, more particularly phenyl or naphthyl, said heteroaryl or aryl groups being optionally substituted by one or more groups, more particularly by one or two groups, selected from the halogen atoms, more particularly fluorine, and the ($C_1$-$C_4$)alkyl groups, more particularly methyl, ($C_1$-$C_4$)alkoxy, more particularly methoxy, aryl, more particularly phenyl.

Among the compounds of formula (I) covered by the invention, a third subgroup of compounds comprises compounds for which:

$R_1$ represents a heteroaryl group, more particularly a furanyl, thienyl, pyrrolyl, pyrazolyl, triazolyl, imidazolyl, indolyl, indazolyl, benzothienyl, azaindolyl, said heteroaryl group being optionally substituted by one or more groups, more particularly by one or two groups, selected from the halogen atoms, more particularly fluorine, and the ($C_1$-$C_4$)alkyl groups, more particularly methyl, ($C_1$-$C_4$)alkoxy, more particularly methoxy, aryl, more particularly phenyl.

Among the compounds of formula (I) covered by the invention, a fourth subgroup of compounds comprises compounds for which:

$R_2$ represents a hydrogen atom.

Among the compounds of formula (I) covered by the invention, a fifth subgroup of compounds comprises compounds for which:

$R_3$ represents a group —($CH_2$)n-$NR_4R_5$ in which n is equal to 2, 3 or 4, and $R_4$ and $R_5$ represent, independently of one another, a ($C_1$-$C_4$)alkyl group, more particularly methyl or ethyl, or alternatively $R_4$ and $R_5$ form together, with the nitrogen atom which carries them, a ($C_3$-$C_7$)heterocycloalkyl group, more particularly pyrrolidinyl or piperidinyl; or a group —($CH_2$)m$R_6$ in which m is equal to 0, 1, 2, 3 or 4, more particularly 0 or 2, and $R_6$ represents a ($C_3$-$C_7$)heterocycloalkyl group containing at least one nitrogen atom and bound to the triazine ring by a carbon atom, more particularly pyrrolidinyl or quinuclidinyl, the ($C_3$-$C_7$)heterocycloalkyl group being optionally substituted by one or more ($C_1$-$C_4$)alkyl groups, more particularly methyl;

with the condition that, when $R_1$ represents a phenyl, $R_4$ and $R_5$ do not represent a methyl simultaneously.

Among the compounds of formula (I) covered by the invention, a sixth subgroup of compounds comprises compounds for which, simultaneously $R_1$ is as defined in the first, the second or the third subgroup above;

$R_2$ is as defined in the fourth subgroup above;

$R_3$ is as defined in the fifth subgroup above.

Among the compounds of formula (I) covered by the invention, a seventh subgroup of compounds comprises compounds for which:

$R_1$ represents an indolyl group, said indolyl group being optionally substituted by one or more groups, more particularly by one or two groups, selected from the halogen atoms, more particularly, fluorine and chlorine, and the ($C_1$-$C_4$)alkyl groups, more particularly methyl, ($C_1$-$C_4$) alkoxy, more particularly methoxy, ($C_3$-$C_7$)cycloalkyl, more particularly cyclohexyl, aryl, more particularly phenyl, —$NH_2$, —$NO_2$; and/or $R_2$ represents a hydrogen atom; and/or $R_3$ represents a group —($CH_2$)n-$NR_4R_5$ in which n is equal to 2, 3 or 4, and $R_4$ and $R_5$ represent, independently of one another, a ($C_1$-$C_4$)alkyl group, more particularly methyl or ethyl, or alternatively $R_4$ and $R_5$ form, together with the nitrogen atom which carries them, a ($C_3$-$C_7$)heterocycloalkyl group, more particularly pyrrolidinyl or piperidinyl; or a group —($CH_2$)m$R_6$ in which m is equal to 0, 1, 2, 3 or 4, more particularly 0 or 2, and $R_6$ represents a ($C_3$-$C_7$)heterocycloalkyl group, more particularly pyrrolidinyl or quinuclidinyl, the ($C_3$-$C_7$) heterocycloalkyl group being optionally substituted by one or more ($C_1$-$C_4$)alkyl groups, more particularly methyl.

Among the compounds of formula (I) covered by the invention, we may mention notably the following compounds:

6-(1-methyl-1H-indol-3-yl)-3-(3-piperidin-1-yl-propylamino)-4H-1,2,4-triazin-5-one 3-(3-diethylamino-propylamino)-6-(1-methyl-1H-indol-3-yl)-4H-1,2,4-triazin-5-one 3-(3-diethylamino-propylamino)-6-phenyl-4H-1,2,4-triazin-5-one 3-(2-diethylamino-ethylamino)-6-(1-methyl-1H-indol-3-yl)-4H-1,2,4-triazin-5-one 3-(3-dimethylamino-propylamino)-6-(1-methyl-1H-indol-3-yl)-4H-1,2,4-triazin-5-one 6-(1-methyl-1H-indol-3-yl)-3-(3-pyrrolidin-1-yl-propylamino)-4H-1,2,4-triazin-5-one 6-(1-methyl-1H-indol-3-yl)-3-[2-(1-methyl-pyrrolidin-2-yl)-ethylamino]-4H-1,2,4-triazin-5-one 6-(1H-indol-3-yl)-3-(3-pyrrolidin-1-yl-propylamino)-4H-1,2,4-triazin-5-one 6-(1H-indol-3-yl)-3-(3-piperidin-1-yl-propylamino)-4H-1,2,4-triazin-5-one 3-[(S)-(1-aza-bicyclo[2.2.2]oct-3-yl)amino]-6-(1H-indol-3-yl)-4H-1,2,4-triazin-5-one 3-[(R)-(1-aza-bicyclo[2.2.2]oct-3-yl)amino]-6-(1H-indol-3-yl)-4H-1,2,4-triazin-5-one)

6-(furan-3-yl)-3-(3-diethylaminopropylamino)-4H-1,2,4-triazin-5-one)

6-(naphth-1-yl)-3-(3-diethylaminopropylamino)-4H-1,2,4-triazin-5-one 6-(1-methyl-5-methoxy-indol-3-yl)-3-(3-diethylaminopropylamino)-4H-1,2,4-triazin-5-one 6-(1-phenyl-indol-3-yl)-3-(3-diethylaminopropylamino)-4H-1,2,4-triazin-5-one 6-(indol-3-yl)-3-(3-diethylaminopropylamino)-4H-1,2,4-triazin-5-one 6-(benzothiophen-3-yl)-3-(3-diethylaminopropylamino)-4H-1,2,4-triazin-5-one 6-(4-methoxyphenyl)-3-(3-diethylaminopropylamino)-4H-1,2,4-triazin-5-one 6-(1-methyl-5-fluoro-indol-3-yl)-3-(3-diethylaminopropylamino)-4H-1,2,4-triazin-5-one 6-(1-methyl-6-fluoro-indol-3-yl)-3-(3-diethylaminopropylamino)-4H-1,2,4-triazin-5-one 6-(3-methoxyphenyl)-3-(3-diethylaminopropylamino)-4H-1,2,4-triazin-5-one 6-(4-(4-methylphenyl))-3-(3-diethylaminopropylamino)-4H-1,2,4-triazin-5-one 6-(1-methyl-4-fluoro-indol-3-yl)-3-(3-diethylaminopropylamino)-4H-1,2,4-triazin-5-one.

In accordance with the invention, the compounds of general formula (I) can be prepared according to the methods illustrated by the schemes given hereunder.

A first method of preparation of the compounds of general formula (I) is shown in scheme 1.

According to this method, the compound of general formula (II), in which $R_1$ is as defined in general formula (I), is condensed hot with thiosemicarbazide in the presence of water and in a concentrated acid medium, to obtain the compound of general formula (III).

The compound of general formula (III) is then cyclized hot in a basic medium, for example in the presence of sodium hydroxide, to form the compound of general formula (IV).

The compound of general formula (V) is then obtained by methylation of the compound of general formula (IV) in the presence of methyl iodide and a strong base such as sodium hydride in a solvent such as dimethylformamide (DMF). Finally, the compound of general formula (I) is obtained by reaction of the compound of general formula (V) with an amine of general formula $HNR_2R_3$ (VI), in which $R_2$ and $R_3$ are as defined in general formula (I).

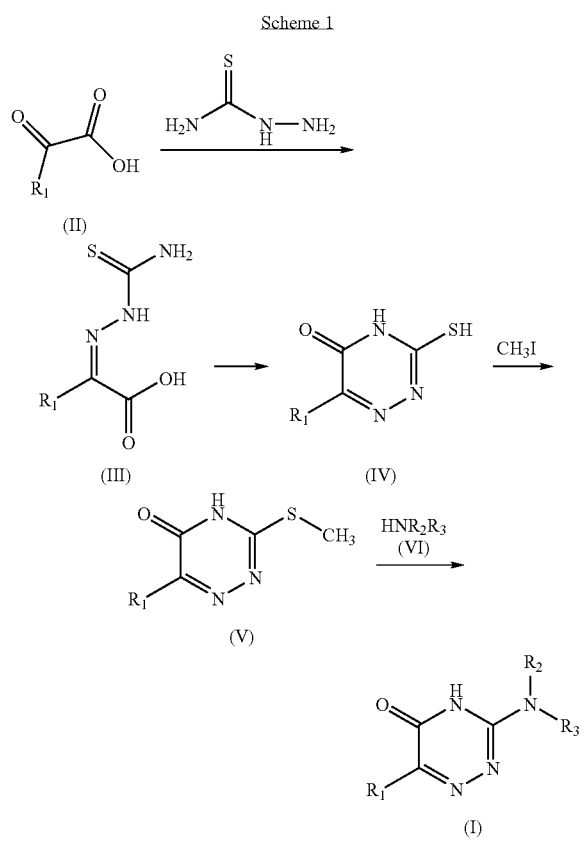

A second method of preparation of the compounds of general formula (I) is shown in scheme 2. According to this method, thiosemicarbazide is first methylated in the presence of methyl iodide in a solvent such as ethanol. The resulting methylated product is then brought into contact with an amine of general formula $HNR_2R_3$ (VI), in which $R_2$ and $R_3$ are as defined in general formula (I), in a solvent such as ethanol, to form the compound of general formula (VII). Finally, the compound of general formula (I) is obtained by reaction of the compound of general formula (VII) with the compound of general formula (II), in which $R_1$ is as defined in general formula (I), in water, heating for example with microwaves to a temperature of the order of 140° C.

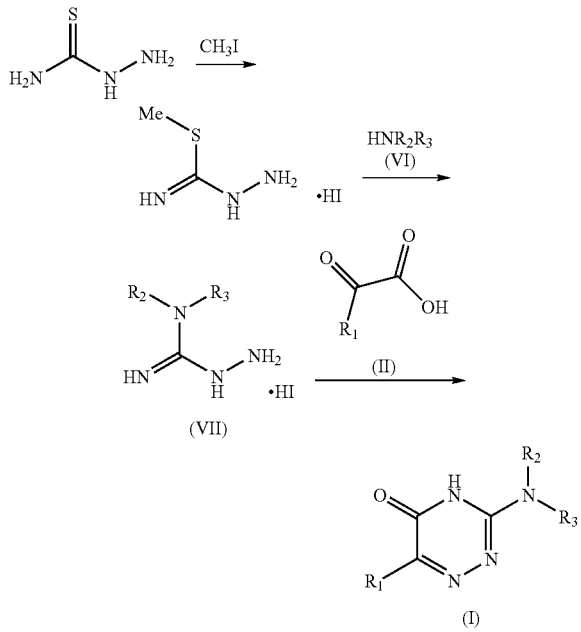

The compounds of general formula (II) are commercially available, known in the literature or can be prepared by methods familiar to a person skilled in the art. The compounds of general formula (II) or the corresponding esters can be synthesized for example by application or adaptation of the methods described in Tetrahedron Lett., 1994, 35 (19), 3013-3016, Tetrahedron Lett., 1998, 39 (52), 9629-9630, J. Org. Chem., 2002, 67 (17), 6226-6227, Synthesis, 1998 (9), 1241-1242, J. Heterocycl. Chem., 1997, 34 (2), 441-444, J. Heterocycl. Chem., 1997, 34 (3), 789-795, Tetrahedron, 2003, 59 (7), 1083-1094, Bioorg. Med. Chem. Lett., 2002, 12 (7), 1117-1120, Heterocycles, 1998, 49 (1), 459-464, J. Org. Chem., 1981, 46 (1), 211-213, Tetrahedron, 1196, 52 (42), 13513-13520, Tetrahedron, 1999, 55 (37), 11343-11364, J. Org. Chem., 1987, 52 (26), 5733-5740, Adv. Synth. Catal., 2001, 343 (3), 289-298 or Tetrahedron Lett., 1983, 24 (33), 3455-3456. The optional transformation of the ester of a compound of general formula (II) to a compound of general formula (II) is carried out according to the conventional methods familiar to a person skilled in the art.

The compounds of general formula (VI) are commercially available, known in the literature or can be prepared by methods familiar to a person skilled in the art. The compounds of general formula (VI) can be synthesized for example by application or adaptation of the methods described in WO2003018585A1, WO2002085901A1, WO2003029252A1, Synth. Comm., 2002, 32 (13), 1985-1995, WO2002068420A1, EP115933A2, J. Med. Chem., 1993, 36 (6), 683-689, Tetrahedron, 1992, 49 (2), 451-468, Hev. Chim. Acta, 1955, 38 (3), 559-570, Hev. Chim. Acta 1959, 42 (1), 67-72, J. Med. Chem., 1993, 36 (16), 2311-20, WO2003070728A2, or J. Org. Chem., 1996, 61 (11), 3766-3772.

In schemes 1 and 2, the starting compounds and the reagents, when their manner of preparation is not described, are commercially available or described in the literature, or alternatively can be prepared according to methods that are described in the literature or are known by a person skilled in the art.

The following examples describe the preparation of some compounds according to the invention. These examples are not limiting and only serve to illustrate the present invention. The numbers of the compounds in the examples refer to those in the table given hereunder, which shows the chemical structures and physical properties of some compounds according to the invention.

EXAMPLE 1

6-(1-methyl-1H-indol-3-yl)-3-(3-piperidin-1-yl-propylamino)-4H-1,2,4-triazin-5-one (Compound No. 2)

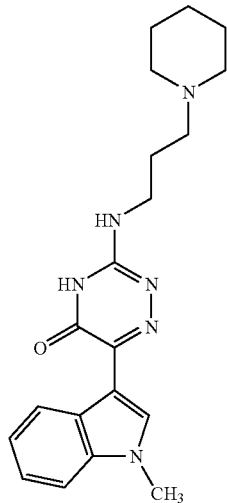

1.1 3-mercapto-6-(1-methyl-1H-indol-3-yl)-4H-1,2,4-triazin-5-one

Add 2.25 cm³ of 12N hydrochloric acid to a suspension of 15 g of (1-methyl-1H-indol-3-yl)-oxo-acetic acid and 7.8 g of thiosemicarbazide in 150 cm³ of water and heat the mixture with stirring for 2.5 h at 100° C. Cool the reaction mixture in an iced-water bath and filter the suspended solid, rinse with water and dry in air. After taking up the yellow solid obtained (20.5 g) in 150 cm³ of water and adjusting the pH of the solution to a pH close to 11 with 1N sodium hydroxide, heat the mixture under reflux for 4 h with stirring and continue stirring for 15 h at a temperature close to 20° C. The reaction mixture, cooled on an ice bath, is brought to a pH close to 4 by adding acetic acid. The resulting precipitate is collected by filtration, rinsed with water and dried in air for 3 days to give 18.9 g of 3-mercapto-6-(1-methyl-1H-indol-3-yl)-4H-1,2,4-triazin-5-one in the form of a yellow solid.

1.2 6-(1-methyl-1H-indol-3-yl)-3-methylsulfanyl-4H-1,2,4-triazin-5

Add a solution of 10 g of 3-mercapto-6-(1-methyl-1H-indol-3-yl)-4H-1,2,4-triazin-5-one, prepared in stage 1.1, in 75 cm³ of dimethylformamide, to a suspension of 1.35 g of sodium hydride (at 75% in vaseline oil) in 25 cm³ of dimethylformamide under an argon atmosphere and with stirring. After 1 h of reaction at a temperature close to 20° C., add 2.4 cm³ of methyl iodide to the reaction mixture, then stir for 15 h at a temperature close to 20° C. Addition of 50 cm³ of water to the mixture causes appearance of a precipitate, which is collected by filtration, rinsed three times with water and dried in air. The solid obtained is triturated in diisopropyl ether, collected by filtration and dried under reduced pressure (2.7 kPa) to give 8.3 g of 6-(1-methyl-1H-indol-3-yl)-3-methylsulfanyl-4H-1,2,4-triazin-5-one in the form of a yellow solid. ¹H-NMR spectrum (300 MHz)—δ in ppm—in DMSO-d₆: 2.56 (s, 3H); 3.90 (s, 3H); from 7.17 to 7.35 (m, 2H); 7.56 (d broad, J=7.5 Hz, 1H); 8.33 (d broad, J=7.5 Hz, 1H); 8.73 (s, 1H); from 13.6 to 14.1 (m very spread-out, 1H)

1.3 6-(1-methyl-1H-indol-3-yl)-3-(3-piperidin-1-yl-propylamino)-4H-1,2,4-triazin-5-one A mixture of 780 mg of 6-(1-methyl-1H-indol-3-yl)-3-methylsulfanyl-4H-1,2,4-triazin-5-one, prepared in stage 1.2, and of 1 g of 3-piperidin-1-yl-propylamine is heated under an argon atmosphere with stirring for 24 h at 130° C., then it is cooled to a temperature close to 20° C. and poured into ice water. The precipitate that forms is solubilized by adding 1N hydrochloric acid. The mixture is re-alkalized by adding 1N sodium hydroxide. The solid which precipitates is collected by filtration and crystallized in methanol. After collecting the crystals by filtration and drying under reduced pressure (2.7 kPa), 260 mg of 6-(1-methyl-1H-indol-3-yl)-3-(3-piperidin-1-yl-propylamino)-4H-1,2,4-triazin-5-one is obtained in the form of a gray solid. Mass spectrum (IC): m/z=367 (MH⁺, base peak). ¹H-NMR spectrum (300 MHz)—δ in ppm—in DMSO-d₆: 1.44 (m, 2H); 1.60 (m, 4H); 1.71 (m, 2H); from 2.29 to 2.42 (m, 6H); 3.26 (m, 2H); 3.86 (s, 3H); 7.10 (m spread-out, 1H); 7.16 (t broad, J=7.5 Hz, 1H); 7.25 (t broad, J=7.5 Hz, 1H); 7.51 (d broad, J=7.5 Hz, 1H); 8.34 (d broad, J=7.5 Hz, 1H); 8.63 (s, 1H).

EXAMPLE 2

3-(3-diethylamino-propylamino)-6-(1-methyl-1H-indol-3-yl)-4H-1,2,4-triazin-5-one (Compound No. 1)

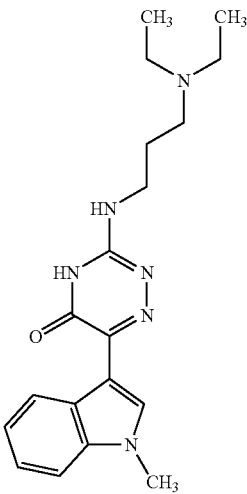

Prepare 3-(3-diethylamino-propylamino)-6-(1-methyl-1H-indol-3-yl)-4H-1,2,4-triazin-5-one according to a procedure identical to that described in Example 1, but replacing, in stage 1.3, the 3-piperidin-1-yl-propylamine with N1,N1-diethyl-propane-1,3-diamine. $^1$H-NMR spectrum (400 MHz)—δ in ppm—in DMSO-$d_6$ referenced to 2.50 ppm: 0.98 (t, J=6.5 Hz, 6H); 1.66 (m, 2H); from 2.40 to 2.57 (m partially masked, 6H); 3.27 (m partially masked, 2H); 3.85 (s, 3H); 7.08 (t broad, J=6.5 Hz, 1H); 7.18 (t, J=8.0 Hz, 1H); 7.24 (t, J=8.0 Hz, 1H); 7.49 (d, J=8.0 Hz, 1H); 8.32 (d, J=8.0 Hz, 1H); 8.60 (s, 1H).

EXAMPLE 3

3-(3-diethylamino-propylamino)-6-phenyl-4H-1,2,4-triazin-5-one (Compound No. 20)

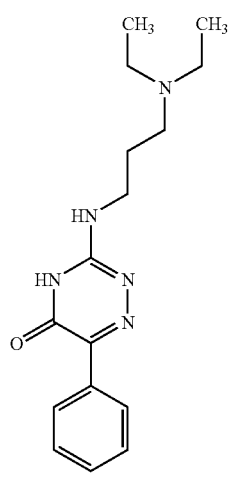

3.1 3-mercapto-6-phenyl-4H-1,2,4-triazin-5-one

Add 0.88 cm³ of 12N hydrochloric acid to a suspension of 10 g of oxo-phenyl-acetic acid and 7 g of thiosemicarbazide in 150 cm³ of water and heat the mixture with stirring for 2.5 h with reflux of the reaction mixture. After cooling the mixture in a bath of ice water, collect the suspended solid by filtration, rinse with water and dry in air. After taking up the pale yellow solid obtained (15.5 g) in 150 cm³ of water and adjusting the mixture to a pH close to 14 with 1N sodium hydroxide, heat the mixture for 4 h with stirring and with reflux of the reaction mixture, cool it on an ice bath, and adjust the pH to 4 by adding acetic acid. The resulting precipitate is collected by filtration, rinsed with water and dried on a screen for 2 days to give 11.3 g of 3-mercapto-6-phenyl-4H-1,2,4-triazin-5-one in the form of a pale yellow solid. Mass spectrum (IE): m/z=205 (M$^{+\cdot}$, base peak), m/z=118 ((M-$C_2HNOS)^+$), m/z=104 ($C_7H_6N^+$).

3.2
3-methylsulfanyl-6-phenyl-4H-1,2,4-triazin-5-one

Add a solution of 11.3 g of 3-mercapto-6-phenyl-4H-1,2,4-triazin-5-one, prepared in stage 3.1, in 120 cm³ of dimethylformamide, to a suspension of 1.96 g of sodium hydride (at 75% in vaseline oil) in 70 cm³ of dimethylformamide under an argon atmosphere and with stirring. After 1 h of reaction at a temperature close to 20° C., add 3.45 cm³ of methyl iodide to the reaction mixture, stir for 15 h at a temperature close to 20° C., then pour into 200 cm³ of water. Cooling the mixture in ice causes crystallization of a compound which is collected by filtration and dried in air to give 7.6 g of 3-methylsulfanyl-6-phenyl-4H-1,2,4-triazin-5-one in the form of a pale yellow solid. Mass spectrum (IE): m/z=219 (M$^{+\cdot}$), m/z=172 ((M-$CH_3S)^+$), m/z=104 ($C_7H_6N^+$, base peak).

3.3 3-(3-diethylamino-propylamino)-6-phenyl-4H-1,2,4-triazin-5-one

A mixture of 900 mg of 3-methylsulfanyl-6-phenyl-4H-1,2,4-triazin-5-one, prepared in stage 3.2, and of 1.65 cm³ of N1,N1-diethyl-propane-1,3-diamine is heated under an argon atmosphere with stirring for 15 h at 100° C., then it is cooled to a temperature close to 20° C. and poured into ice water. The precipitate formed by acidification of the mixture to pH close to 4 with 1N hydrochloric acid is removed by filtration. The filtrate is brought to pH close to 11 by adding 1N soda and it is extracted twice with dichloromethane. The resulting aqueous phase is neutralized with 1N hydrochloric acid and it is extracted twice with dichloromethane. The organic phases are combined, dried over magnesium sulfate, filtered and concentrated under reduced pressure (2.7 kPa) to give a yellow oil (170 mg) which is purified by flash chromatography on alumina CTB1 under argon pressure (50 kPa) [eluent: dichloromethane/methanol (95/5 by volume)]. After concentrating the fractions under reduced pressure, we get 115 mg of 3-(3-diethylamino-propylamino)-6-phenyl-4H-1,2,4-triazin-5-one in the form of a cream-colored solid. Mass spectrum (IC): m/z=302 (MH$^+$, base peak). $^1$H-NMR spectrum (300 MHz)—δ in ppm—in DMSO-$d_6$+1 drop of acetic acid-$d_4$: 1.20 (t, J=7.5 Hz, 6H); from 1.80 to 1.95 (m masked, 2H); from 3.05 to 3.19 (m, 6H); 3.35 (t, J=6.5 Hz, 2H); 7.41 (m, 3H); 7.96 (m, 2H).

EXAMPLE 4

3-(2-diethylamino-ethylamino)-6-(1-methyl-1H-indol-3-yl)-4H-1,2,4-triazin-5-one (Compound No. 17)

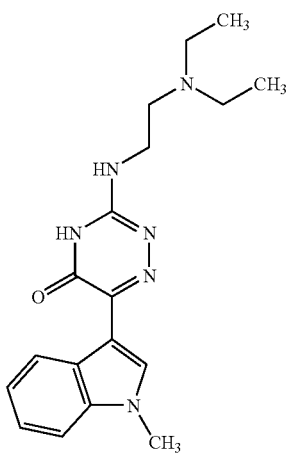

A mixture of 1 g of 6-(1-methyl-1H-indol-3-yl)-3-methylsulfanyl-4H-1,2,4-triazin-5-one, prepared according to stage 1.2 of Example 1, and 1.3 cm³ of N1,N1-diethyl-ethane-1,2-diamine is heated under an argon atmosphere with stirring for 15 h at 130° C., then it is cooled to a temperature close to 20° C. The raw reaction product is purified by flash chromatography on alumina CTB1 under argon pressure (50 kPa) [eluent: dichloromethane, then dichloromethane/methanol (98/2 by volume)]. After concentrating the fractions under reduced pressure (2.7 kPa), we get a residue which is triturated in diisopropyl ether, collected by filtration and dried under reduced pressure to give 150 mg of 3-(2-diethylamino-ethylamino)-6-(1-methyl-1H-indol-3-yl)-4H-1,2,4-triazin-5-one in the form of a cream-colored solid. Mass spectrum (IE): m/z=340 (M$^{+\cdot}$), m/z=241 ((M-C$_6$H$_{13}$N)$^+$), m/z=86 (C$_5$H$_{12}$N$^+$., base peak). $^1$H-NMR spectrum (300 MHz)—δ in ppm—in DMSO-d$_6$+1 drop of acetic acid-d$_4$: 1.10 (m, 6H); from 2.72 to 2.90 (m, 6H); 3.42 (m, 2H); 3.85 (s, 3H); 7.18 (t broad, J=7.5 Hz, 1H); 7.26 (t broad, J=7.5 Hz, 1H); 7.52 (d broad, J=7.5 Hz, 1H); 8.32 (d broad, J=7.5 Hz, 1H); 8.62 (s, 1H).

EXAMPLE 5

3-(3-dimethylamino-propylamino)-6-(1-methyl-1H-indol-3-yl)-4H-1,2,4-triazin-5-one (Compound No. 14)

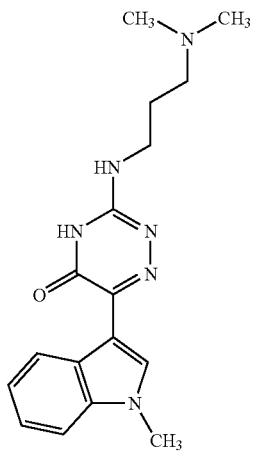

A mixture of 1 g of 6-(1-methyl-1H-indol-3-yl)-3-methylsulfanyl-4H-1,2,4-triazin-5-one, prepared according to stage 1.2 of Example 1, and 1.15 cm$^3$ of N1,N1-dimethyl-propane-1,3-diamine is heated under an argon atmosphere with stirring for 15 h at 130° C., then it is cooled to a temperature close to 20° C., 1N hydrochloric acid is added so that the pH of the mixture is close to 4 and extracted with dichloromethane which is discarded. The aqueous phase P is brought to a pH close to 8 by adding 1N soda, then it is extracted twice with dichloromethane. The organic phase is dried over magnesium sulfate and concentrated under reduced pressure (2.7 kPa). The oil residue obtained is purified by flash chromatography on alumina CTB1 under argon pressure (50 kPa) [eluent: dichloromethane, then dichloromethane/methanol (98/2 by volume)]. After concentrating the fractions under reduced pressure, we get a solid R1 (250 mg). The aqueous phase P is alkalized to a pH close to 10 by adding 1N soda and it is extracted twice with dichloromethane. The organic phase is dried over magnesium sulfate and concentrated under reduced pressure (2.7 kPa) to give a solid R2 (330 mg). The solids R1 and R2 are combined, triturated hot in diisopropyl ether, collected by filtration while hot and dried under reduced pressure to give 550 mg of 3-(3-dimethylamino-propylamino)-6-(1-methyl-1H-indol-3-yl)-4H-1,2,4-triazin-5-one in the form of a pale yellow solid. Mass spectrum (IE): m/z=326 (M$^{+\cdot}$), m/z=282 ((M-C$_2$H$_6$N)$^{+\cdot}$), m/z=156 (C$_{11}$H$_{10}$N$^+$), m/z=58 (C$_3$H$_8$N$^+$, base peak). $^1$H-NMR spectrum (300 MHz)—δ in ppm—in DMSO-d$_6$: 1.69 (m, 2H); 2.19 (s, 6H); 2.32 (t, J=6.5 Hz, 2H); 3.29 (m, 2H); 3.85 (s, 3H); 7.08 (t very broad, J=6.0 Hz, 1H); 7.17 (t broad, J=7.5 Hz, 1H); 7.26 (t broad, J=7.5 Hz, 1H); 7.51 (d broad, J=7.5 Hz, 1H); 8.33 (d broad, J=7.5 Hz, 1H); 8.62 (s, 1H).

EXAMPLE 6

6-(1-methyl-1H-indol-3-yl)-3-(3-pyrrolidin-1-yl-propylamino)-4H-1,2,4-triazin-5-one (Compound No. 8)

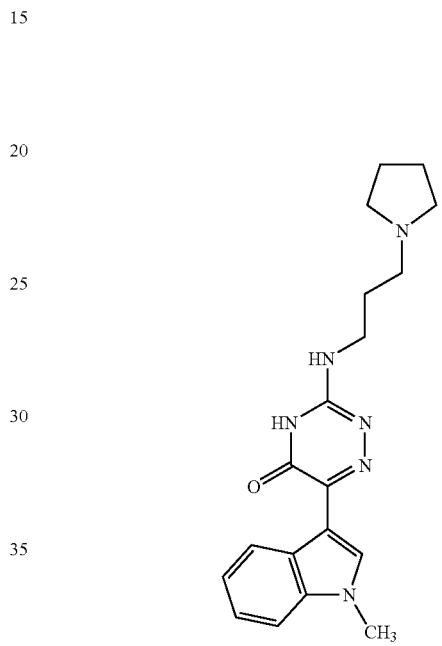

A mixture of 1.1 g of 6-(1-methyl-1H-indol-3-yl)-3-methylsulfanyl-4H-1,2,4-triazin-5-one, prepared according to stage 1.2 of Example 1, and 1.5 cm$^3$ of 3-pyrrolidin-1-yl-propylamine is heated under an argon atmosphere with stirring for 15 h at 150° C., then it is cooled to a temperature close to 20° C., triturated in ethyl acetate and filtered. The residue is taken up in 10 cm$^3$ of ethanol and the mixture is held under reflux. The suspension is filtered while hot, the residue is rinsed twice with ethanol and dried under reduced pressure (2.7 kPa) to give 690 mg of 6-(1-methyl-1H-indol-3-yl)-3-(3-pyrrolidin-1-yl-propylamino)-4H-1,2,4-triazin-5-one in the form of a beige solid. Mass spectrum (IE): m/z=352 (M$^{+\cdot}$), m/z=282 ((M-C$_4$H$_8$N)$^{+\cdot}$), m/z=156 (C$_{11}$H$_{10}$N$^+$), m/z=110 (C$_7$H$_{12}$N$^+$, base peak), m/z=84 (C$_5$H$_{10}$N$^+$). $^1$H-NMR spectrum (300 MHz)—δ in ppm—in DMSO-d$_6$: From 1.64 to 1.82 (m, 6H); from 2.44 to 2.55 (partially masked, 6H); 3.30 (masked, 2H); 3.86 (s, 3H); 7.05 (t very broad, J=6.0 Hz, 1H); 7.16 (t broad, J=7.5 Hz, 1H); 7.25 (t broad, J=7.5 Hz, 1H); 7.50 (d broad, J=7.5 Hz, 1H); 8.32 (d broad, J=7.5 Hz, 1H); 8.63 (s, 1H).

EXAMPLE 7

6-(1-methyl-1H-indol-3-yl)-3-[2-(1-methyl-pyrrolidin-2-yl)-ethylamino]-4H-1,2,4-triazin-5-one (Compound No. 15)

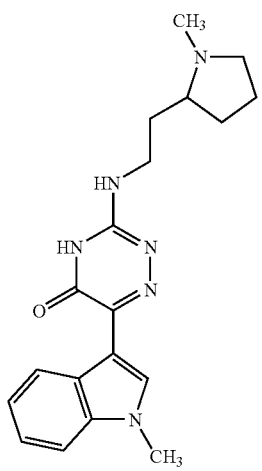

A mixture of 1.1 g of 6-(1-methyl-1H-indol-3-yl)-3-methylsulfanyl-4H-1,2,4-triazin-5-one, prepared according to stage 1.2 of Example 1, and 1.9 cm³ of 2-(1-methyl-pyrrolidin-2-yl)-ethylamine is heated under an argon atmosphere with stirring for 15 h at 140° C., then it is cooled to a temperature close to 20° C., taken up in ethyl acetate and water, and stirred for 15 min at a temperature close to 20° C. The organic phase is decanted, washed three times with water and once with brine, then it is dried over magnesium sulfate and concentrated under reduced pressure (2.7 kPa) to give an orange-colored oil (850 mg) which is purified by flash chromatography on alumina CTB1 under argon pressure (50 kPa) [eluent: ethyl acetate/methanol (97/3 by volume)]. After evaporating the fractions under reduced pressure (2.7 kPa), we get a solid which is purified once again by flash chromatography on alumina CTB1 under argon pressure (50 kPa) [eluent: ethyl acetate/methanol (90/10 by volume)]. Concentration of the appropriate fractions under reduced pressure (2.7 kPa) gives a residue which is triturated in diisopropyl ether, collected by filtration and dried under reduced pressure (2.7 kPa) to give 80 mg of 6-(1-methyl-1H-indol-3-yl)-3-[2-(1-methyl-pyrrolidin-2-yl)-ethylamino]-4H-1,2,4-triazin-5-one in the form of a beige solid. Mass spectrum (IE): m/z=352 (M$^{+\cdot}$), m/z=156 ($C_{11}H_{10}N^+$), m/z=110 ($C_7H_{12}N^+$, base peak), m/z=84 ($C_5H_{10}N^+$). $^1$H-NMR spectrum (300 MHz)—δ in ppm—in DMSO-d$_6$+1 drop of acetic acid-d$_4$: from 1.65 to 2.40 (m, 6H); 2.84 (s, 3H); 3.10 (m, 1H); from 3.25 to 3.45 (m, 3H); 3.54 (m, 1H); 3.85 (s, 3H); 7.17 (t broad, J=7.5 Hz, 1H); 7.25 (t broad, J=7.5 Hz, 1H); 7.50 (d broad, J=7.5 Hz, 1H); 8.30 (d broad, J=7.5 Hz, 1H); 7.61 (s, 1H)

EXAMPLE 8

6-(1H-indol-3-yl)-3-(3-pyrrolidin-1-yl-propylamino)-4H-1,2,4-triazin-5-one (Compound No. 10)

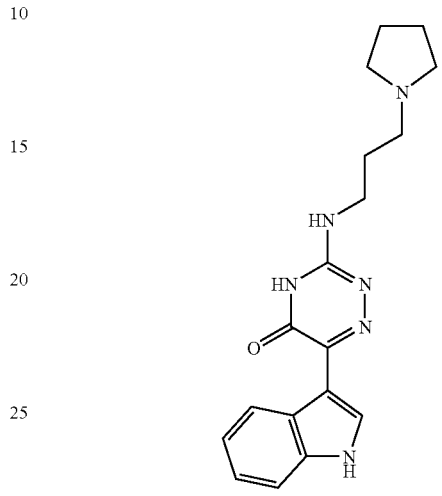

8.1 S-methyl-thiosemicarbazide hydroiodide

Add 14 cm³ of methyl iodide dropwise, at a temperature close to 20° C., to a solution of 20 g of thiosemicarbazide in 70 cm³ of methanol, with stirring. Continue stirring for 3.5 h at the same temperature then concentrate the reaction mixture to dryness under reduced pressure (2.7 kPa). The residue is triturated three times in succession in dichloromethane, collected by filtration and dried under reduced pressure (2.7 kPa), to give 47.9 g of S-methyl-thiosemicarbazide hydroiodide in the form of a solid. Mass spectrum (IE): m/z=128 (IH$^{+\cdot}$, base peak), m/z=105 (M$^{+\cdot}$), m/z=58 ((M-CH$_3$S)$^+$).

8.2 N-(3-pyrrolidin-1-yl-propyl)-hydrazinecarboximidamide hydroiodide

A mixture of 1.99 g of S-methyl-thiosemicarbazide hydroiodide, prepared in stage 8.1, and 1 g of 3-pyrrolidin-1-yl-propylamine in 30 cm³ of ethanol is stirred for 5 days at a temperature close to 20° C. The reaction mixture is concentrated to dryness under reduced pressure (2.7 kPa), triturated in ethyl ether, filtered and dried under reduced pressure (2.7 kPa) to give 2.3 g of N-(3-pyrrolidin-1-yl-propyl)-hydrazinecarboximidamide hydroiodide in the form of a solid. Mass spectrum (IC): m/z=186 (MH$^+$), m/z=129 ((M-CH$_4$N$_3$+2H)$^+$, base peak).

8.3 6-(1H-indol-3-yl)-3-(3-pyrrolidin-1-yl-propylamino)-4H-1,2,4-triazin-5-one A solution of 0.55 g of (1H-indol-3-yl)-oxo-acetic acid and 1 g of N-(3-pyrrolidin-1-yl-propyl)-hydrazinecarboximidamide hydroiodide, prepared in stage 8.2, in 3.5 cm³ of water is placed in a reactor. After sealing the tube, the mixture is submitted to discontinuous microwave irradiation for 10 min so that the temperature of the mixture is maintained at 140° C. Then cool the reaction mixture to a temperature close to 20°

C., add ethanol and concentrate to dryness under reduced pressure (2.7 kPa) to give a residue which is purified by flash chromatography on silica under argon pressure (50 kPa) [eluent: dichloromethane/methanol/ammonia 32% (90/10/1, then 95/15/1.5 by volume)]. After concentrating the fractions under reduced pressure (2.7 kPa), we get 108 mg of 6-(1H-indol-3-yl)-3-(3-pyrrolidin-1-yl-propylamino)-4H-1,2,4-triazin-5-one in the form of a solid. Mass spectrum (ES): m/z=339 (MH+, base peak). $^1$H-NMR spectrum (400 MHz)—δδ in ppm—in DMSO-$d_6$: From 1.65 to 1.85 (m, 6H); 2.57 (m, 6H); 3.30 (m masked, 2H); from 7.05 to 7.20 (m, 3H); 7.46 (d broad, J=8.5 Hz, 1H); 8.30 (d broad, J=8.0 Hz, 1H); 8.63 (d, J=2.5 Hz, 1H); 11.45 (m broad, 1H).

EXAMPLE 9

6-(1H-indol-3-yl)-3-(3-piperidin-1-yl-propylamino)-4H-1,2,4-triazin-5-one (Compound No. 9)

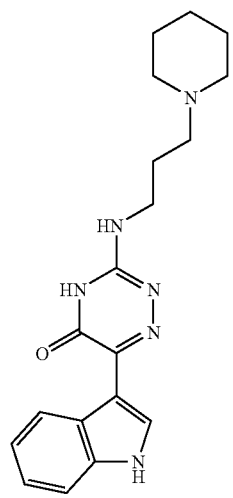

9.1 N-(3-piperidin-1-yl-propyl)-hydrazinecarboximidamide hydroiodide

A mixture of 2 g of S-methyl-thiosemicarbazide hydroiodide, prepared according to stage 8.1 of Example 8, and 1.22 g of 3-piperidin-1-yl-propylamine in 30 cm$^3$ of ethanol is stirred for 6 days at a temperature close to 20° C. The reaction mixture is concentrated to dryness under reduced pressure (2.7 kPa), and triturated three times in succession in ethyl ether, filtered and dried under reduced pressure (2.7 kPa), to give 2.6 g of N-(3-piperidin-1-yl-propyl)-hydrazinecarboximidamide hydroiodide in the form of a solid. Mass spectrum (IE): m/z=199 (M+·), m/z=168 ((M-N$_2$H$_3$)+), m/z=128 (IH+·, base peak), m/z=98 ($C_6H_{12}N^+$).

9.2 6-(1H-indol-3-yl)-3-(3-piperidin-1-yl-propylamino)-4H-1,2,4-triazin-5-one

A solution of 0.55 g of (1H-indol-3-yl)-oxo-acetic acid and 1.04 g of N-(3-piperidin-1-yl-propyl)-hydrazinecarboximidamide hydroiodide, prepared in stage 9.1, in 3.5 cm$^3$ of water is placed in a reactor. After sealing the tube, the mixture is submitted to discontinuous microwave irradiation for 10 min so that the temperature of the mixture is maintained at 140° C. Then cool the reaction mixture to a temperature close to 20° C., add ethanol and evaporate to dryness under reduced pressure (2.7 kPa) to give a residue which is purified by flash chromatography on silica under argon pressure (50 kPa) [eluent: dichloromethane/methanol/ammonia 32% (90/10/1 by volume)]. After concentrating the fractions under reduced pressure (2.7 kPa), we get 35 mg of 6-(1H-indol-3-yl)-3-(3-piperidin-1-yl-propylamino)-4H-1,2,4-triazin-5-one in the form of a solid. Mass spectrum (ES): m/z=353 (MH+, base peak). $^1$H-NMR spectrum (300 MHz)—δ in ppm—in DMSO-$d_6$: From 1.15 to 1.85 (m spread-out, 6H); 1.95 (m, 2H); from 2.80 to 3.55 (m spread-out, 8H); from 7.05 to 7.22 (m, 3H); 7.47 (d broad, J=8.0 Hz, 1H); 8.31 (d broad, J=8.0 Hz, 1H); 8.62 (d, J=2.5 Hz, 1H); from 8.95 to 9.15 (m spread-out, 1H); 11.45 (m broad, 1H); 12.3 (m spread-out, 1H).

EXAMPLE 10

Hydrated hydrochloride of 3-[(S)-(1-aza-bicyclo[2.2.2]oct-3-yl)amino]-6-(1H-indol-3-yl)-4H-1,2,4-triazin-5-one (Compound No. 6)

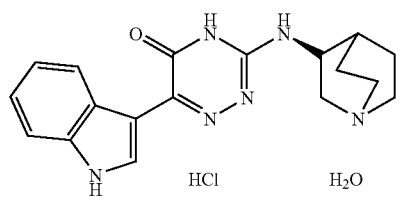

10.1 (S)—N-(1-aza-bicyclo[2.2.2]oct-3-yl)-hydrazinecarboximidamide hydroiodide

A mixture of 2.77 g of S-methyl-thiosemicarbazide hydroiodide, prepared according to stage 8.1 of Example 8, and 1.5 g of (S)-(1-aza-bicyclo[2.2.2]oct-3-yl)amine in 25 cm$^3$ of ethanol is stirred for 6 days at a temperature close to 20° C. The reaction mixture is concentrated to dryness under reduced pressure (2.7 kPa), and the residue is triturated in ethyl ether, collected by filtration and dried under reduced pressure (2.7 kPa), to give 3.2 g of (S)—N-(1-aza-bicyclo[2.2.2]oct-3-yl)-hydrazinecarboximidamide hydroiodide in the form of a solid which is used without further purification in the next stage.

10.2 Hydrated hydrochloride of 3-[(S)-(1-aza-bicyclo[2.2.2]oct-3-yl)amino]-6-(1H-indol-3-yl)-4H-1,2,4-triazin-5-one A solution of 0.55 g of (1H-indol-3-yl)-oxo-acetic acid and 1.2 g of (S)—N-(1-aza-bicyclo[2.2.2]oct-3-yl)-hydrazinecarboximidamide hydroiodide, prepared in stage 10.1, in 3 cm$^3$ of water is placed in a reactor. After sealing the tube, the mixture is submitted to discontinuous microwave irradiation for 10 min so that the temperature of the mixture is maintained at 140° C. Then cool the reaction mixture to a temperature close to 20° C., add methanol and evaporate to dryness under reduced pressure (2.7 kPa) to give a residue which is purified by flash chromatography on silica under argon pressure (50 kPa) [eluent: dichloromethane/methanol/ammonia 32% (75/22/3 by volume)]. After concentrating the fractions under reduced pressure (2.7 kPa), we get a solid which is washed successively with dichloromethane and ethyl ether, then dried under reduced pressure (2.7 kPa) to give 74 mg of hydrated hydrochloride of 3-[(S)-(1-aza-bicyclo[2.2.2]oct-3-yl)amino]-6-(1H-indol-3-yl)-4H-1,2,4-triazin-5-one in the form of a yellow solid. Mass spectrum (IE): m/z=336 (M+·, base peak), m/z=252 ((M-C$_5$H$_{10}$N)+·), m/z=227 ((M-C$_7$H$_{11}$N)+), m/z=109 (C$_7$H$_{11}$N+·), m/z=36 (HCl+·). $^1$H-NMR spectrum (400 MHz)—δ in ppm—in DMSO-d$_6$ referenced to 2.50 ppm: 1.66 (m, 1H); 1.83 (m, 2H); 2.00 (m, 1H); 2.12 (m, 1H); 2.93 (m, 1H); from 3.00 to 3.19 (m, 4H); 3.54 (m, 1H); 4.10 (m, 1H); 7.10 (t, J=8.0 Hz, 1H); 7.17 (t, J=8.0 Hz, 1H); 7.46 (d, J=8.0 Hz, 1H); 7.66 (d broad, J=7.0 Hz, 1H); 8.29 (d, J=8.0 Hz, 1H); 8.60 (d, J=2.0 Hz, 1H); 11.5 (s broad, 1H); of 11.9 to 12.4 (m very spread-out, 1H). [α]$^{20}_D$=−24.5+/−0.7° (c 0.42, methanol).

EXAMPLE 11

Hydrochloride of 3-[(R)-(1-aza-bicyclo[2.2.2]oct-3-yl)amino]-6-(1H-indol-3-yl)-4H-1,2,4-triazin-5-one (Compound No. 13)

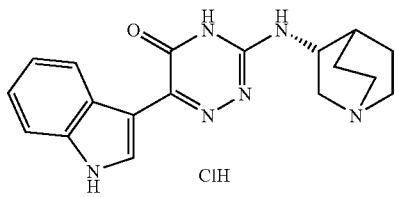

11.1 (R)—N-(1-aza-bicyclo[2.2.2]oct-3-yl)-hydrazinecarboximidamide hydroiodide

A mixture of 1 g of S-methyl-thiosemicarbazide hydroiodide, prepared according to stage 8.1 of Example 8, 0.89 g of (R)-(1-aza-bicyclo[2.2.2]oct-3-yl)amine dihydrochloride and 1.2 cm$^3$ of triethylamine in 20 cm$^3$ of ethanol is stirred for 6 days at a temperature close to 20° C. The reaction mixture is concentrated to dryness under reduced pressure (2.7 kPa), and the residue is triturated in ethyl ether, collected by filtration and dried under reduced pressure (2.7 kPa), to give 1.25 g of (R)—N-(1-aza-bicyclo[2.2.2]oct-3-yl)-hydrazinecarboximidamide hydroiodide in the form of a solid. Mass spectrum (ES): m/z=184 (MH+), m/z=127 ((M-CH$_4$N$_3$+2H)+), m/z=102 ((M-C$_5$H$_9$N+2H)+), base peak).

11.2 Hydrochloride of 3-[(R)-(1-aza-bicyclo[2.2.2]oct-3-yl)amino]-6-(1H-indol-3-yl)-4H-1,2,4-triazin-5-one A solution of 0.55 g of (1H-indol-3-yl)-oxo-acetic acid and 1.22 g of (R)—N-(1-aza-bicyclo[2.2.2]oct-3-yl)-hydrazinecarboximidamide hydroiodide, prepared in stage 11.1, in 3 cm$^3$ of water is placed in a reactor. After sealing the tube, the mixture is submitted to discontinuous microwave irradiation for 20 min so that the temperature of the mixture is maintained at 140° C. Then cool the reaction mixture to a temperature close to 20° C., add methanol and evaporate to dryness under reduced pressure (2.7 kPa) to give a residue which is purified by flash chromatography on silica under argon pressure (50 kPa) [eluent: dichloromethane/methanol/ammonia 32% (75/22/3 by volume)]. After concentrating the fractions under reduced pressure (2.7 kPa), we get a residue which is washed successively with dichloromethane and ethyl ether, then dried under reduced pressure (2.7 kPa). The solid obtained is treated on a BOND ELUT VARIAN cartridge containing 2 g of SCX phase conditioned beforehand with methanol (eluent: methanol, then 2N ammoniacal methanol) and the appropriate fractions are evaporated under reduced pressure (2.7 kPa) to give a residue which is dissolved in ethanol and a 1N solution of hydrochloric acid in ethyl ether is added. The precipitate that forms is collected by filtration, washed with ethyl ether and dried under reduced pressure (2.7 kPa). We get 60 mg of hydrochloride of 3-[(R)-(1-aza-bicyclo[2.2.2]oct-3-yl)amino]-6-(1H-indol-3-yl)-4H-1,2,4-triazin-5-one in the form of an orange-colored solid. Mass spectrum (ES): m/z=337 (MH+). $^1$H-NMR spectrum (400 MHz)—δ in ppm—in DMSO-d$_6$ referenced to 2.50 ppm: 1.79 (m, 1H); 1.92 (m, 2H); 2.10 (m, 1H); 2.22 (m, 1H); 3.11 (m, 1H); from 3.17 to 3.32 (m, 4H); from 3.60 to 3.90 (m partially masked, 1H); 4.22 (m, 1H); 7.11 (t, J=8.0 Hz, 1H); 7.18 (t, J=8.0 Hz, 1H); 7.46 (d, J=8.0 Hz, 1H); 7.90 (d broad, J=6.0 Hz, 1H); 8.30 (d, J=8.0 Hz, 1H); 8.60 (d, J=2.0 Hz, 1H); 9.92 (s broad, 1H); 11.5 (s broad, 1H); from 12.2 to 12.5 (m spread-out, 1H).

EXAMPLE 12

6-(furan-3-yl)-3-(3-diethylaminopropylamino)-4H-1,2,4-triazin-5-one (Compound No. 23)

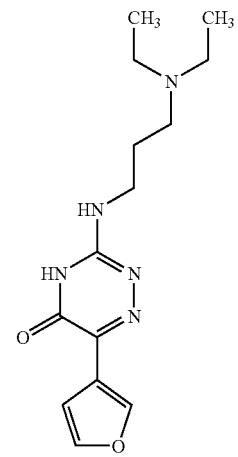

12.1 N-amino-N'-(3-diethylaminopropyl)-guanidine hydroiodide

A mixture of 18.38 g of S-methyl-thiosemicarbazide hydroiodide, prepared according to stage 8.1 of Example 8, and 9.45 cm$^3$ of 3-(diethylamino)propylamine in 180 cm$^3$ of ethanol is stirred at a temperature close to 20° C. for 48 h. The orange-colored solution is concentrated under reduced pressure (2.7 kPa). The residue is taken up in ethyl ether and the supernatant is removed. Repeat this operation twice then make a paste of the solid residue with ethyl ether and dry it to give 17.36 g of N-amino-N'-(3-diethylaminopropyl)-guanidine hydroiodide.

12.2 6-(furan-3-yl)-3-(3-diethylaminopropylamino)-4H-1,2,4-triazin-5-one

A mixture of 473 mg of N-amino-N'-(3-diethylamino-propyl)-guanidine hydroiodide, prepared in stage 12.1, and 210 mg of furan-3-yl-oxo-acetic acid in 3 cm$^3$ of water, is heated for 10 min at 140° C. in a microwave oven then it is cooled to a temperature close to 20° C. and 15 cm³ of dichloromethane and 5 cm³ of 1N soda are added. After decanting, the organic phase is drawn off and the aqueous phase is re-extracted twice with 15 cm³ of dichloromethane. The organic phases are combined, washed with water, dried over magnesium sulfate, filtered and concentrated to dryness under reduced pressure (2.7 kPa). We get 1.4 g of a raw product which is purified by chromatography on silica 60 (40-63 μm) under argon pressure (50 kPa) [eluent: dichloromethane, then dichloromethane/methanol/ammonia 32% (90/9/1 by volume)] to give 0.185 g of a pale yellow solid, which is then taken up in ether, dried, washed with a minimum of ether, then dried under reduced pressure (2.7 kPa) at 40° C. In this way we get 0.155 g of a pale yellow powder. Mass spectrum (ES): m/z=292 (MH⁺); ¹H-NMR spectrum (300 MHz)—δ in ppm—in DMSO-d₆: 1.00 (t, J=7.5 Hz, 6H); 1.67 (m, 2H); from 2.42 to 2.60 (m, 6H); 3.27 (m, 2H); 6.84 (d, J=2.0 Hz, 1H); 7.24 (m spread-out, 1H); 7.74 (t, J=2.0 Hz, 1H); 8.53 (d, J=2.0 Hz, 1H).

phase is re-extracted twice with 15 cm³ of dichloromethane. The organic phases are combined, washed with water, dried over magnesium sulfate, filtered and concentrated under reduced pressure. We get 0.384 g of a raw product, which is purified by chromatography on silica 60 (40-63 μm) [eluent: dichloromethane, then dichloromethane/methanol/ammonia (85/14/1 by volume)] to give 0.058 g of a pale yellow solid, which is then taken up in ether, dried, washed with a minimum of ether and dried under reduced pressure (2.7 kPa) at 40° C. We get 0.048 g of 6-(naphthalen-1-yl)-3-(3-diethylaminopropylamino)-4H-1,2,4-triazin-5-one in the form of a white powder. Mass spectrum (ES): m/z=352 (MH⁺); ¹H-NMR spectrum (300 MHz)—δ in ppm—in DMSO-d₆: 1.17 (t, J=7.5 Hz, 6H); 1.90 (m, 2H); from 2.40 to 3.00 (m partially masked, 6H); 3.42 (m, 2H); 7.12 (m spread-out, 1H); from 7.44 to 7.60 (m, 4H); 7.80 (d broad, J=7.5 Hz, 1H); 7.98 (m, 2H).

EXAMPLE 13

6-(naphthalen-1-yl)-3-(3-diethylaminopropylamino)-4H-1,2,4-triazin-5-one (Compound No. 21)

EXAMPLE 14

6-(1-methyl-5-methoxy-indol-3-yl)-3-(3-diethylaminopropylamino)-4H-1,2,4-triazin-5-one hydroiodide (Compound No. 22)

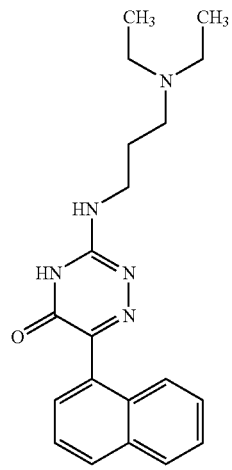

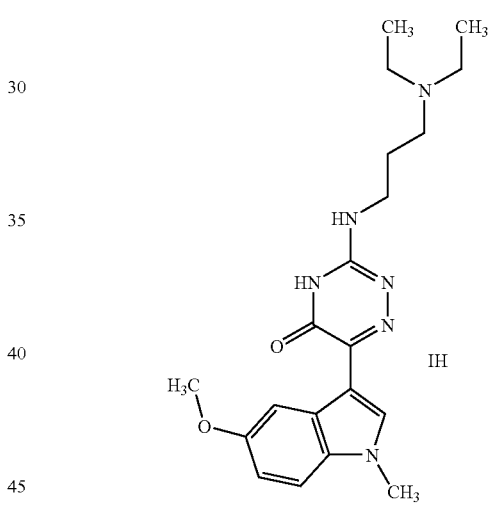

13.1 Sodium naphthalen-1-yl-oxo-acetate

A two-phase mixture of 0.912 g of ethyl naphthoylformate and 4 cm³ of 1N soda in 4 cm³ of water is heated at a temperature close to 70° C. for 2 h, during which the mixture becomes homogeneous, then it is filtered on Acrodisc® Gelman 0.45 μm. The filtrate is lyophilized to give 0.855 g of sodium naphthalen-1-yl-oxo-acetate in the form of a white powder.

13.2 6-(naphthalen-1-yl)-3-(3-diethylaminopropylamino)-4H-1,2,4-triazin-5-one A mixture of 640 mg of N-amino-N'-(3-diethylaminopropyl)-guanidine hydroiodide, prepared in stage 12.1 of Example 12, and 0.44 g of sodium naphthalen-1-yl-oxo-acetate, prepared in stage 13.1, in 0.5 cm³ of acetic acid and 2 cm³ of water, is heated for 10 min at 140° C. in a microwave oven, then it is cooled to a temperature close to 20° C., diluted with 15 cm³ of dichloromethane and 10 cm³ of 1N soda and decanted. The organic phase is drawn off and the aqueous A mixture of 472 mg of N-amino-N'-(3-diethylamino-propyl)-guanidine hydroiodide, prepared in stage 12.1 of Example 12, and 349 mg of (5-methoxy-1-methyl-1H-indol-3-yl)-oxo-acetic acid in 3 cm³ of water and 0.5 cm³ of dioxan is heated for 10 min at 140° C. in a microwave oven, then it is cooled to a temperature close to 20° C. and evaporated to dryness under reduced pressure (2.7 kPa). We get 810 mg of a chestnut-brown solid which is purified by chromatography on silica 60 (40-63 μm) [eluent: dichloromethane, then dichloromethane/methanol/ammonia 32% (85/14/1 by volume)] to give 0.157 g of a yellow solid which is then taken up in methanol, dried, washed with a minimum of methanol and dried under reduced pressure (2.7 kPa) at 40° C. We get 0.087 g of 6-(1-methyl-5-methoxy-indol-3-yl)-3-(3-diethylaminopropylamino)-4H-1,2,4-triazin-5-one hydroiodide in the form of a yellow powder. Mass spectrum (ES): m/z=385 (MH⁺); ¹H-NMR spectrum (300 MHz)—δ in ppm—in DMSO-d₆: 1.22 (t, J=7.5 Hz, 6H); 1.92 (m, 2H); 3.13 (m, 6H); 3.34 (m masked, 2H); 3.81 (s, 3H); 3.83 (s, 3H); 6.92 (dd, J=2.5 and 9.0 Hz, 1H); 7.13 (m spread-out, 1H); 7.43 (d, J=9.0

Hz, 1H); 7.84 (d, J=2.5 Hz, 1H); 8.60 (s, 1H); 9.15 (m spread-out, 1H); 12.3 (m very spread-out, 1H).

EXAMPLE 15

6-(1-phenyl-indol-3-yl)-3-(3-diethylaminopropy-lamino)-4H-1,2,4-triazin-5-one (Compound No. 11)

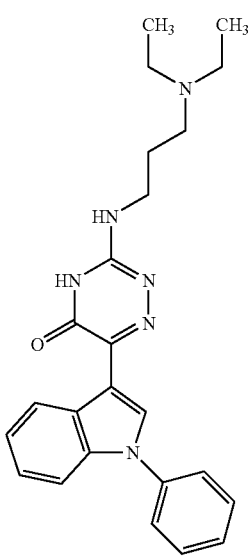

15.1 1-phenyl-1H-indole

A mixture of 1.17 g of indole, 1.6 cm³ of bromobenzene, 112 mg of palladium acetate, 333 mg of 1,1'-bis(diphenylphosphino)ferrocene and 1.44 g of sodium tert-butylate in 20 cm³ of toluene is heated for 48 h under reflux. The suspension, of a dark-chestnut color, is diluted with 50 cm³ of ethyl acetate and 10 cm³ of water. The insoluble matter is filtered and the two phases are decanted. The aqueous phase is re-extracted with ethyl acetate, the organic phases are combined and washed with a saturated solution of ammonium chloride, dried over sodium sulfate, filtered and concentrated to dryness under reduced pressure (2.7 kPa). The chestnut-colored oil (1.85 g) obtained is purified by chromatography on silica 60 (40-63 μm) [eluent: heptane/ethyl acetate (90/10 by volume)] to give 0.375 g of 1-phenyl-1H-indole in the form of a pale yellow solid.

15.2 Oxo-(1-phenyl-1H-indol-3-yl)-acetic acid

A solution of 0.368 cm³ of oxalyl chloride in 2 cm³ of ether is added dropwise, at a temperature close to 0° C., to a solution of 0.35 g of 1-phenyl-1H-indole, prepared in stage 15.1, in 16 cm³ of ether. Leave the reaction mixture to return to a temperature close to 20° C. and stir the mixture for 3 h at this temperature. The reaction mixture is then brought to pH 8 with 1N soda and it is extracted with ethyl acetate. The aqueous phase is acidified to pH 2 with concentrated hydrochloric acid. The precipitates formed are collected by filtration, washed with water and ether, and dried under reduced pressure (2.7 kPa) at 40° C. to give 0.352 g of oxo-(1-phenyl-1H-indol-3-yl)-acetic acid.

15.3 6-(1-phenyl-indol-3-yl)-3-(3-diethylaminopropylamino)-4H-1,2,4-triazin-5-one A mixture of 458 mg of N-amino-N'-(3-diethylamino-propyl)-guanidine hydroiodide, prepared in stage 12.1 of Example 12, and 340 mg of oxo-(1-phenyl-1H-indol-3-yl)-acetic acid, prepared in stage 15.2, in 4 cm³ of water is heated for 10 min at 140° C. in a microwave oven, then it is cooled to a temperature close to 20° C., diluted with 15 cm³ of dichloromethane and 5 cm³ of 1N soda, and decanted. The organic phase is drawn off and the aqueous phase is re-extracted twice with 15 cm³ of dichloromethane. The organic phases are combined and washed with water, dried over magnesium sulfate, filtered and concentrated to dryness under reduced pressure (2.7 kPa). We get 0.3 g of a yellow residue which is purified by chromatography on silica 60 (40-63 μm) [eluent: dichloromethane/methanol/ammonia 32% (90/9/1 by volume)] to give 0.135 g of 6-(1-phenyl-indol-3-yl)-3-(3-diethylaminopropylamino)-4H-1,2,4-triazin-5-one in the form of a pale yellow solid. Mass spectrum (ES): m/z=417 (MH⁺), 344 (M-C₄H₁₁N+H⁺). ¹H-NMR spectrum (300 MHz)—δ in ppm—in DMSO-d₆: 1.01 (t, J=7.5 Hz, 6H); 1.70 (m, 2H); from 2.44 to 2.55 (m partially masked, 6H); 3.31 (m, 2H); from 7.14 to 7.34 (m, 3H); from 7.45 to 7.70 (m, 6H); 8.45 (dd, J=1.5 and 7.5 Hz, 1H); 8.85 (s, 1H).

EXAMPLE 16

6-(indol-3-yl)-3-(3-diethylaminopropylamino)-4H-1,2,4-triazin-5-one (Compound No. 7)

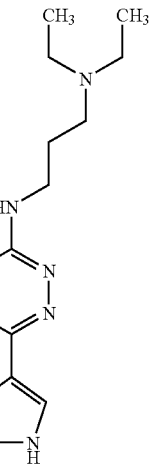

16.1 (1H-indol-3-yl)-oxo-acetic acid

A mixture of 610 mg of methyl indolyl-3-glyoxylate and 3.3 cm³ of 1N soda in 3.3 cm³ of water is heated for 1 h at 80° C., then it is cooled on an ice bath and 3.5 cm³ of 1N hydrochloric acid is added. The mixture is extracted with ethyl acetate. The organic phases are combined and dried over sodium sulfate, filtered and concentrated to dryness under reduced pressure (2.7 kPa) to give 554 mg of (1H-indol-3-yl)-oxo-acetic acid in the form of a yellow solid.

16.2 6-(indol-3-yl)-3-(3-diethylaminopropylamino)-4H-1,2,4-triazin-5-one

A mixture of 350 mg of N-amino-N'-(3-diethylamino-propyl)-guanidine hydroiodide, prepared in stage 12.1 of Example 12, and 189 mg of (1H-indol-3-yl)-oxo-acetic acid, prepared in stage 16.1, in 4 cm³ of water is heated for 15 min at 140° C. in a microwave oven, then it is cooled to a temperature close to 20° C. and diluted with ethyl acetate and water. The aqueous phase is extracted with ethyl acetate, ethyl acetate is added, then it is alkalized with 2N soda. The organic phase is drawn off and the aqueous phase is re-extracted with ethyl acetate. The organic phases are combined and dried over magnesium sulfate, filtered and concentrated to dryness under reduced pressure (2.7 kPa). The residue is triturated in ethyl acetate, collected by filtration and the solid (83 mg) is dried, made into a paste in methanol, then dried. The product obtained (50 mg) is purified by chromatography on silica, [eluent: dichloromethane/methanol/ammonia 32% (90/9/1, 90/10/0.5, then 85/15/1 by volume)] to give 0.044 g of 6-(indol-3-yl)-3-(3-diethylaminopropylamino)-4H-1,2,4-triazin-5-one in the form of a pale yellow solid. Mass spectrum (ES): m/z=341 (MH$^+$); $^1$H-NMR spectrum (400 MHz)—δ in ppm—in DMSO-d$_6$: 1.01 (t, J=7.5 Hz, 6H); 1.69 (m, 2H); from 2.38 to 2.55 (m partially masked, 6H); 3.30 (partially masked, 2H); from 7.03 to 7.21 (m, 3H); 7.46 (d broad, J=8.0 Hz, 1H); 8.32 (d broad, J=8.0 Hz, 1H); 8.64 (d, J=2.0 Hz, 1H); 11.5 (m broad, 1H).

EXAMPLE 17

6-(benzothiophen-3-yl)-3-(3-diethylaminopropylamino)-4H-1,2,4-triazin-5-one (Compound No. 12)

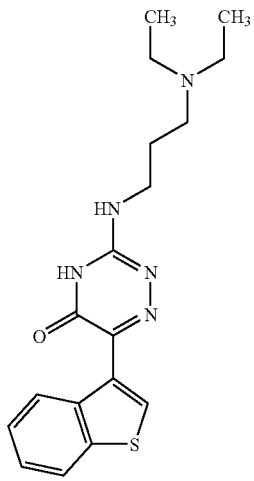

17.1 Ethyl benzo[b]thiophen-3-yl-oxo-acetate

To a solution, under nitrogen and cooled to −10° C., of 8.34 cm³ of oxalyl chloride in 140 cm³ of dichloromethane, add in succession 10.54 g of aluminum chloride, then, in 2 h, a solution of 10 g of benzothiophene in 100 cm³ of dichloromethane. The temperature is maintained at −10° C. throughout the addition, then stirring is continued for about 1 h at a temperature close to 20° C. The reaction mixture is then poured into ice water and a saturated solution of double tartrate of potassium and sodium is added, causing aluminum salts to be precipitated. The suspension is filtered on Hyflo-supercel® Kieselguhr and decanted. The organic phase is drawn off and the aqueous phase is re-extracted with dichloromethane. The organic phases are combined and washed with water, dried over sodium sulfate and concentrated to dryness under reduced pressure (2.7 kPa). The residue is purified by chromatography on silica [eluent: dichloromethane/heptane (70/30 by volume)] to give 10.78 g of ethyl benzo[b]thiophen-3-yl-oxo-acetate in the form of an orange-colored oil.

17.2 6-(benzothiophen-3-yl)-3-(3-diethylaminopropylamino)-4H-1,2,4-triazin-5-one A mixture of 469 mg of ethyl benzo[b]thiophen-3-yl-oxo-acetate, prepared in stage 17.1, and 2 cm³ of 1N soda in 2 cm³ of water is stirred for 15 min at a temperature close to 20° C., then heated to 70° C. for 30 min. The reaction mixture is brought to a temperature close to 20° C., then it is transferred to a microwave container. 700 mg of N-amino-N'-(3-diethylamino-propyl)-guanidine hydroiodide, prepared in stage 12.1 of Example 12, is added to the mixture, then it is heated at 140° C. for 10 min. The reaction mixture is concentrated under reduced pressure (2.7 kPa), then it is purified by chromatography on silica [eluent: dichloromethane/methanol/ammonia 32% (90/9/1, 90/10/0.5, then 85/15/1 by volume)] to give 0.045 g of 6-(benzothiophen-3-yl)-3-(3-diethylaminopropylamino)-4H-1,2,4-triazin-5-one in the form of a pale yellow solid. Mass spectrum (ES): m/z=357 (MH$^+$); $^1$H-NMR spectrum (400 MHz)—δ in ppm—in DMSO-d$_6$: 1.01 (t, J=7.5 Hz, 6H); 1.70 (m, 2H); from 2.42 to 2.59 (m partially masked, 6H); 3.30 (m, 2H); from 7.30 to 7.50 (m, 3H); 8.06 (d broad, J=8.0 Hz, 1H); 8.54 (d broad, J=8.0 Hz, 1H); 8.92 (s, 1H).

EXAMPLE 18

6-(4-methoxyphenyl)-3-(3-diethylaminopropylamino)-4H-1,2,4-triazin-5-one (Compound No. 18)

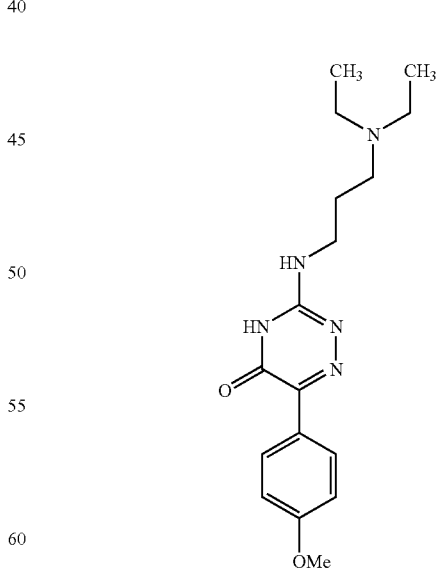

18.1 Sodium (4-methoxy-phenyl)-oxo-acetate

A mixture of 1.041 g of ethyl 4-methoxybenzoate and 5 cm³ of 1N soda in 5 cm³ of water is heated at 80° C. for 1 h, then it is cooled and lyophilized to give 1 g of sodium (4-methoxy-phenyl)-oxo-acetate.

18.2 6-(4-methoxyphenyl)-3-(3-diethylaminopropylamino)-4H-1,2,4-triazin-5-one A mixture of 700 mg of N-amino-N'-(3-diethylamino-propyl)-guanidine hydroiodide, prepared in stage 12.1 of Example 12, and 400 mg of sodium (4-methoxy-phenyl)-oxo-acetate prepared in stage 18.1, in 4 cm³ of water is heated for 15 min at 140° C. in a microwave oven and then cooled to a temperature close to 20° C. The reaction mixture is dried under reduced pressure (2.7 kPa) and the residue is purified by chromatography on silica [eluent: dichloromethane/methanol/ammonia 32% (90/9/1 by volume)] to give a solid which is made into a paste in ethyl acetate and dried. We get 0.092 g of 6-(4-methoxyphenyl)-3-(3-diethylaminopropylamino)-4H-1,2,4-triazin-5-one in the form of a white solid. Mass spectrum (ES): m/z=332 (MH⁺), 259 (M-C₄H₁₁N+H⁺); ¹H-NMR spectrum (300 MHz)—δ in ppm—in DMSO-d₆: 0.98 (t, J=7.5 Hz, 6H); 1.66 (m, 2H); from 2.49 to 2.56 (m partially masked, 6H); 3.26 (m, 2H); 3.82 (s, 3H); 6.97 (d broad, J=9.0 Hz, 2H); 7.20 (m spread-out, 1H); 8.01 (d broad, J=9.0 Hz, 2H).

EXAMPLE 19

6-(1-methyl-5-fluoro-indol-3-yl)-3-(3-diethylamino-propylamino)-4H-1,2,4-triazin-5-one (Compound No. 3)

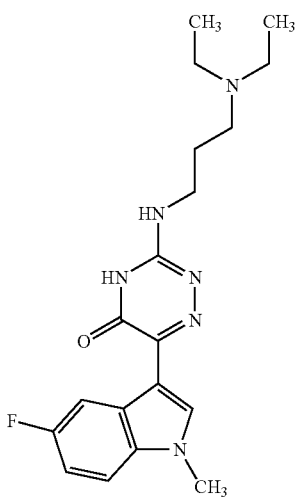

19.1 5-fluoro-1H-indol-3-yl-oxo-acetic acid

A solution of 523 µl of oxalyl chloride in 5 cm³ of ethyl ether is added by syringe in 15 min to a solution of 5-fluor-oindole in 10 cm³ of ethyl ether, maintained between 0° C. and 5° C. The reaction mixture, initially colorless, turns yellow, then a yellow precipitate gradually appears. The suspension is stirred for 1 h 30 min at a temperature close to 20° C., then it is cooled on an ice bath and alkalized with 1N soda. It is stirred until the precipitate dissolves completely. The solution is extracted twice with ethyl acetate. The aqueous phases are combined, acidified with concentrated hydrochloric acid and cooled on an ice bath. The precipitate is collected by filtration, drained and dried under reduced pressure (2.7 kPa) at 50° C. to give 795 mg of 5-fluoro-1H-indol-3-yl-oxo-acetic acid in the form of a pale yellow solid.

19.2 (5-fluoro-1-methyl-1H-indol-3-yl)-oxo-acetic acid

Add 1.01 g of potassium hydroxide in a single portion to a suspension of 622 mg of 5-fluoro-1H-indol-3-yl-oxo-acetic acid, prepared in stage 19.1, in 10 cm³ of acetone, cooled on an ice bath. Leave the mixture to reach a temperature close to 20° C., stir for some minutes at this temperature, cool again with the ice bath then add 757 µl of methyl iodide. After stirring for 15 h at a temperature close to 20° C., the very thick, colorless suspension is diluted with acetone, 373 µl of methyl iodide is added, then it is stirred for a further 1 h at a temperature close to 20° C. Add water to the reaction mixture and stir until completely dissolved. Extract the solution twice with ethyl acetate and wash the organic phase with water. The aqueous phases are combined and acidified with concentrated hydrochloric acid and cooled on an ice bath. The precipitate that forms is collected by filtration and dried under reduced pressure (2.7 kPa) at 50° C. for 15 h to give 517 mg of (5-fluoro-1-methyl-1H-indol-3-yl)-oxo-acetic acid in the form of pale yellow flakes.

19.3 6-(1-methyl-5-fluoro-indol-3-yl)-3-(3-diethylaminopropylamino)-4H-1,2,4-triazin-5-one A mixture of 630 mg of N-amino-N'-(3-diethylamino-propyl)-guanidine hydroiodide, prepared in stage 12.1 of Example 12, and 442 mg of (5-fluoro-1-methyl-1H-indol-3-yl)-oxo-acetic acid, prepared in stage 19.2, in 2 cm³ of water is heated for 15 min at 140° C. in a microwave oven, then cooled to a temperature close to 20° C. The resulting orange mixture is made into a paste with ethanol and filtered. The yellow solid obtained is dried under reduced pressure (2.7 kPa) at 30° C. and it is purified by chromatography on silica [eluent: dichloromethane/methanol/ammonia 32% (80/20/1 by volume)] to give 0.078 g of 6-(1-methyl-5-fluoro-indol-3-yl)-3-(3-diethylaminopropylamino)-4H-1,2,4-triazin-5-one in the form of a white solid. Mass spectrum (ES): m/z=373 (MH⁺), 300 (M-C₄H₁₁N+H⁺). ¹H-NMR spectrum (400 MHz)—δ in ppm—in DMSO-d₆: 1.01 (t, J=7.0 Hz, 6H); 1.68 (m broad, 2H); from 2.43 to 2.58 (m, partially masked, 6H); 3.29 (m, 2H); 3.88 (s, 3H); from 7.09 to 7.20 (m, 2H); 7.54 (dd, J=5.5 and 8.0 Hz, 1H); 8.02 (dd, J=2.0 and 10.5 Hz, 1H); 8.68 (s, 1H).

EXAMPLE 20

6-(1-methyl-6-fluoro-indol-3-yl)-3-(3-diethylamino-propylamino)-4H-1,2,4-triazin-5-one (Compound No. 4)

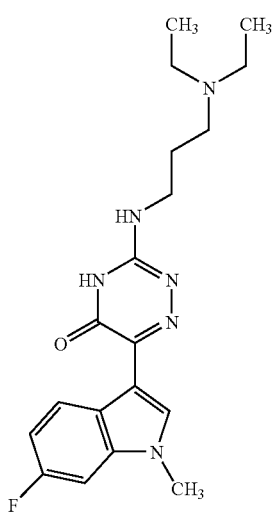

20.1 6-fluoro-1H-indol-3-yl-oxo-acetic acid

A solution of 775 µl of oxalyl chloride in 7 cm³ is added by syringe, in 15 min, to a solution of 1.0 g of 6-fluoroindole in 15 cm³ of ethyl ether, maintained between 0° C. and 5° C. The reaction mixture, initially colorless, turns yellow, then a yellow precipitate gradually forms. The suspension is stirred for 2 h 30 min at a temperature close to 20° C., cooled on an ice bath and alkalized with 1N soda. Stir the mixture until the precipitate has dissolved completely. Extract the solution twice with ethyl acetate. The aqueous phases are combined, acidified with concentrated hydrochloric acid and cooled on an ice bath. The precipitate that forms is collected by filtration then dried under reduced pressure (2.7 kPa) at 50° C. to give 1.12 g of 6-fluoro-1H-indol-3-yl-oxo-acetic acid in the form of a bright yellow solid.

20.2 (6-fluoro-1-methyl-1H-indol-3-yl)-oxo-acetic acid

Add 1.684 g of potassium hydroxide, in a single portion, to a suspension of 1.036 g of 6-fluoro-1H-indol-3-yl-oxo-acetic acid, prepared in stage 20.1, in 17 cm³ of acetone, cooled on an ice bath. Leave the mixture to reach a temperature close to 20° C. and stir for some minutes at this temperature. After cooling the reaction mixture again on the ice bath, add 1.245 cm³ of methyl iodide, allow the mixture to reach a temperature close to 20° C. and stir for 15 h at this temperature. Add 650 µl of iodomethane to the very thick suspension obtained, stir for a further 24 h at a temperature close to 20° C., heat for 30 min under reflux, allow to cool to a temperature close to 20° C. and add water. Stir until completely dissolved, then extract the mixture twice with ethyl acetate. Wash the aqueous phase with water. The aqueous phases are combined and acidified with concentrated hydrochloric acid and cooled on an ice bath. The precipitate is drained and dried under reduced pressure (2.7 kPa) at 50° C. for 15 h to give 1.04 g of (6-fluoro-1-methyl-1H-indol-3-yl)-oxo-acetic acid.

20.3 6-(1-methyl-6-fluoro-indol-3-yl)-3-(3-diethylaminopropylamino)-4H-1,2,4-triazin-5-one A mixture of 630 mg of N-amino-N'-(3-diethylamino-propyl)-guanidine hydroiodide, prepared in stage 12.1 of Example 12, and 442 mg of (6-fluoro-1-methyl-1H-indol-3-yl)-oxo-acetic acid, prepared in stage 20.2, in 2 cm³ of water is heated for 15 min at 140° C. in a microwave oven, then it is cooled to a temperature close to 20° C. The orange mixture obtained is made into a paste with ethanol and the resulting solid is drained and dried under reduced pressure (2.7 kPa) at 40° C., then this solid is purified by chromatography on silica [eluent: dichloromethane/methanol/ammonia 32% (90/10/1 by volume)] to give 0.324 g of 6-(1-methyl-6-fluoro-indol-3-yl)-3-(3-diethylaminopropylamino)-4H-1,2,4-triazin-5-one in the form of a pale yellow solid. Mass spectrum (ES): m/z=373 (MH⁺); $^1$H-NMR spectrum (300 MHz)—δ in ppm—in DMSO-$d_6$: 1.09 (m broad, 6H); 1.77 (m broad, 2H); from 2.40 to 2.86 (m, partially masked, 6H); 3.30 (m masked, 2H); 3.84 (s, 3H); from 6.98 to 7.14 (m, 2H); 7.40 (dd, J=2.5 and 11.0 Hz, 1H); 8.29 (dd, J=5.0 and 9.0 Hz, 1H); 8.62 (s, 1H).

EXAMPLE 21

6-(3-methoxyphenyl)-3-(3-diethylaminopropylamino)-4H-1,2,4-triazin-5-one (Compound No. 16)

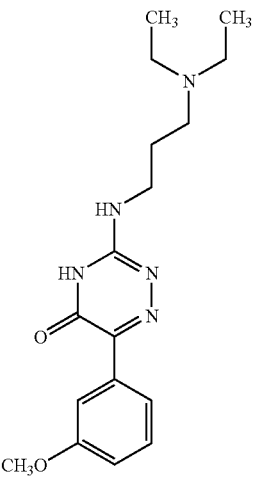

21.1 Ethyl 3-methoxy-phenyl-oxo-acetate

Add 10 cm³ of a 1N solution of 3-methoxyphenylmagnesium bromide in tetrahydrofuran to a mixture, maintained at a temperature between −78° C. and −65° C., of 1.5 cm³ of diethyl oxalate in 10 cm³ of ether. At the end of addition, allow the temperature to rise slowly to 10° C. and neutralize the mixture with a saturated solution of ammonium chloride. Extract the mixture twice with ethyl ether. The organic phases are combined and washed with water, dried over sodium sulfate, filtered and concentrated to dryness under reduced pressure (2.7 kPa). 2.15 g of ethyl 3-methoxy-phenyl-oxo-acetate is isolated as a mixture with about 30% of unreacted diethyl oxalate in the form of a light yellow oil.

21.2 3-methoxy-phenyl-oxo-acetic acid

A mixture of 2.14 g of ethyl 3-methoxy-phenyl-oxo-acetate, prepared in stage 21.1, and 6 cm³ of 2N soda is stirred for 30 min at a temperature close to 20° C. then about 15 cm³ of water is added, which permits the insoluble matter to be dissolved, and it is then stirred for a further 30 min at a temperature close to 20° C. The reaction mixture is extracted with ethyl acetate and the organic phase is washed twice with water. The aqueous phases are combined, acidified with concentrated hydrochloric acid in the presence of ethyl acetate and extracted twice with ethyl acetate. The organic phases are combined, washed twice with water, dried over anhydrous sodium sulfate, filtered, then concentrated to dryness under reduced pressure (2.7 kPa). We get a yellow oil which is dried with a vane pump to give 1.34 g of 3-methoxy-phenyl-oxo-acetic acid.

21.3 6-(3-methoxyphenyl)-3-(3-diethylaminopropylamino)-4H-1,2,4-triazin-5-one A mixture of 630 mg of N-amino-N'-(3-diethylamino-propyl)guanidine hydroiodide, prepared in stage 12.1 of Example 12, and 360 mg of 3-methoxy-phenyl-oxo-acetic acid in 2 cm³ of water is heated for 15 min at 140° C. in a microwave oven, then cooled to a temperature close to 20° C. The reaction mixture is evaporated to dryness under reduced pressure (2.7 kPa) and the residue is purified by chromatography on silica [eluent: dichloromethane/methanol/ammonia 32% (90/10/1 by volume)] to give, after making a paste with ethyl acetate and draining, 0.271 g of 6-(3-methoxyphenyl)-3-(3-diethylaminopropylamino)-4H-1,2,4-triazin-5-one in the form of a white solid. Mass spectrum (ES): m/z=332 (MH⁺); ¹H-NMR spectrum (400 MHz)—δ in ppm—in DMSO-$d_6$: 1.02 (t, J=7.5 Hz, 6H); 1.70 (m, 2H); from 2.45 to 2.66 (m partially masked, 6H); 3.30 (m partially masked, 2H); 3.80 (s, 3H); 7.00 (m, 1H); from 7.25 to 7.36 (m, 2H); 7.59 (m, 2H).

EXAMPLE 22

6-(4-(4-methylphenyl))-3-(3-diethylaminopropylamino)-4H-1,2,4-triazin-5-one (Compound No. 19)

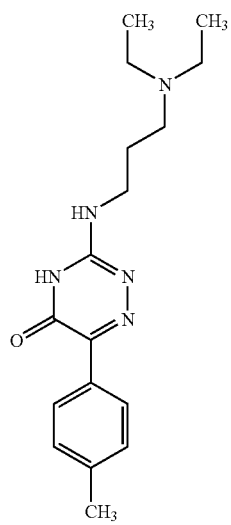

A mixture of 630 mg of N-amino-N'-(3-diethylamino-propyl)-guanidine hydroiodide, prepared in stage 12.1 of Example 12, and 328 mg of 2-(4-methylphenyl)-2-oxo-acetic acid in 2 cm³ of water is heated for 15 min at 140° C. in a microwave oven and then cooled to a temperature close to 20° C. The reaction mixture is evaporated to dryness under reduced pressure (2.7 kPa) and the residue is purified by chromatography on silica [eluent: dichloromethane/methanol/ammonia 32% (85/15/1 by volume)] to give, after making a paste with ethyl ether and draining, 0.467 g of 6-(4-(4-methylphenyl))-3-(3-diethylaminopropylamino)-4H-1,2,4-triazin-5-one in the form of a pale yellow solid. Mass spectrum (ES): m/z=316 (MH⁺), 243 (M—$C_4H_{11}$N+H⁺); ¹H-NMR spectrum (400 MHz)—δ in ppm—in DMSO-$d_6$: 1.21 (t, J=7.5 Hz, 6H); 1.89 (m, 2H); 2.35 (s, 3H); from 3.05 to 3.20 (m, 6H); 3.32 (m masked, 2H); from 6.90 to 7.35 (m very spread-out, 5H); 7.90 (d broad, J=9.0 Hz, 2H).

EXAMPLE 23

6-(1-methyl-4-fluorine-indol-3-yl)-3-(3-diethylaminopropylamino)-4H-1,2,4-triazin-5-one hydroiodide (Compound No. 5)

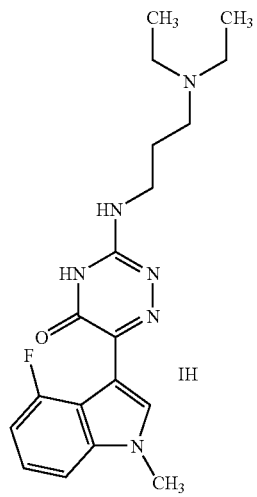

23.1 4-fluoro-1H-indol-3-yl-oxo-acetic acid

Add by syringe, in 15 min, a solution of 800 μl of oxalyl chloride in 7 cm³ of ether to a solution of 1 g of 6-fluoroindole in 15 cm³ of ethyl ether, maintained at a temperature between 0° C. and 50° C. Yellow precipitates form in the reaction mixture. Stir the suspension for 3 h at a temperature close to 20° C., cool on an ice bath and alkalize with 1N soda. Stir until the precipitate has dissolved completely. Extract the solution twice with ethyl acetate. The aqueous phases are combined, acidified with concentrated hydrochloric acid and cooled on an ice bath. The precipitate formed is drained, then dried under reduced pressure (2.7 kPa) at 50° C. to give 892 mg of 4-fluoro-1H-indol-3-yl-oxo-acetic acid in the form of a bright yellow solid.

23.2 (4-fluoro-1-methyl-1H-indol-3-yl)-oxo-acetic acid

Add, in a single portion, 1.443 g of potassium hydroxide to a suspension of 888 mg of 4-fluoro-1H-indol-3-yl-oxo-acetic acid, prepared in stage 23.1, in 15 cm³ of acetone, cooled on an ice bath. Leave to reach a temperature close to 20° C., stir for some minutes at this temperature, cool again on an ice bath then add 1.067 cm³ of methyl iodide. After stirring for 60 h at a temperature close to 20° C., add 550 μl of iodomethane to the very thick suspension obtained and continue stirring the mixture for a further 9 h at a temperature close to 20° C. Extract the reaction mixture twice with ethyl acetate and wash the organic phases with water. The aqueous phases are combined and acidified with concentrated hydrochloric acid and cooled on an ice bath. The precipitate is drained and dried under reduced pressure (2.7 kPa) at 50° C. for 15 h to give 913 mg of (4-fluoro-1-methyl-1H-indol-3-yl)-oxo-acetic acid in the form of a yellowish-brown solid.

23.3 6-(1-methyl-4-fluorine-indol-3-yl)-3-(3-diethylaminopropylamino)-4H-1,2,4-triazin-5-one hydroiodide A mixture of 630 mg of N-amino-N'-(3-diethylamino-propyl)-guanidine hydroiodide, prepared in stage 12.1 of Example 12, and 442 mg of (4-fluoro-1-methyl-1H-indol-3-yl)-oxo-acetic acid, prepared in stage 23.2, in 2 cm³ of water is heated for 15 min at 140° C. in a microwave oven and is then cooled to a temperature close to 20° C. The reaction mixture is evaporated to dryness under reduced pressure (2.7 kPa) and the residue obtained is purified by chromatography on silica [eluent: dichloromethane/methanol/ammonia 32% (85/15/1 by volume)] to give, after making a paste with methanol and draining, 0.150 g of 6-(1-methyl-4-fluorine-indol-3-yl)-3-(3-diethylaminopropylamino)-4H-1,2,4-triazin-5-one hydroiodide in the form of a white solid. Mass spectrum (ES): m/z=373 (MH⁺); ¹H-NMR spectrum (300 MHz)—δ in ppm—in DMSO-d₆: 1.21 (t, J=7.5 Hz, 6H); 1.90 (m, 2H); 3.14 (m, 6H); 3.35 (m partially masked, 2H); 3.87 (s, 3H); 6.87 (dd, J=5.5 and 11.0 Hz, 1H); from 7.05 to 7.37 (m, 3H); 8.18 (s, 1H); from 9.00 to 9.25 (m very spread-out, 1H); 12.4 (m spread-out, 1H).

The following table shows the chemical structures and physical properties of some examples of compounds according to the invention. In this table:

- in the column "salt", "-" denotes a compound in the form of a free base, whereas "HCl", "HCl, H₂O" and "HI" denote, respectively, a compound in the form of hydrochloride, of hydrated hydrochloride and of hydroiodide, and the ratio in parentheses is the ratio (acid:base).
- Et represents an ethyl group.

TABLE

General structure (I): triazin-5-one scaffold with $R_1$ at 6-position, $NR_2R_3$ at 3-position.

| No. | $R_1$ | $R_2$ | $R_3$ | Salt |
|---|---|---|---|---|
| 1 | 1-methyl-1H-indol-3-yl | H | —(CH₂)₃N(Et)₂ | — |
| 2 | 1-methyl-1H-indol-3-yl | H | —(CH₂)₃-piperidin-1-yl | — |
| 3 | 5-fluoro-1-methyl-1H-indol-3-yl | H | —(CH₂)₃N(Et)₂ | — |
| 4 | 6-fluoro-1-methyl-1H-indol-3-yl | H | —(CH₂)₃N(Et)₂ | — |
| 5 | 4-fluoro-1-methyl-1H-indol-3-yl | H | —(CH₂)₃N(Et)₂ | HI (1/1) |
| 6 | 1H-indol-3-yl | H | (S)-quinuclidin-3-yl | HCl, H₂O (1/1/1) |
| 7 | 1H-indol-3-yl | H | —(CH₂)₃N(Et)₂ | — |
| 8 | 1-methyl-1H-indol-3-yl | H | —(CH₂)₃-pyrrolidin-1-yl | — |
| 9 | 1H-indol-3-yl | H | —(CH₂)₃-piperidin-1-yl | — |

TABLE-continued (I) Structure: 6-R₁-3-NR₂R₃-1,2,4-triazin-5(4H)-one

| No. | R₁ | R₂ | R₃ | Salt |
|-----|-----|-----|-----|------|
| 10 | 3-methyl-1H-indol-2-yl | H | 3-(pyrrolidin-1-yl)propyl (ethyl-substituted) | — |
| 11 | 3-methyl-1-phenyl-1H-indol-2-yl | H | —(CH₂)₃N(Et)₂ | — |
| 12 | 3-methylbenzo[b]thiophen-2-yl | H | —(CH₂)₃N(Et)₂ | — |
| 13 | 3-methyl-1H-indol-2-yl | H | (R)-quinuclidin-3-yl | HCl (1/1) |
| 14 | 1,3-dimethyl-1H-indol-2-yl | H | —(CH₂)₃N(CH₃)₂ | — |
| 15 | 1,3-dimethyl-1H-indol-2-yl | CH₃ | 2-(pyrazolidin-1-yl)ethyl | — |
| 16 | 3-methoxyphenyl | H | —(CH₂)₃N(Et)₂ | — |
| 17 | 1-methyl-1H-indol-3-yl | H | —(CH₂)₂N(Et)₂ | — |
| 18 | 4-methoxyphenyl | H | —(CH₂)₃N(Et)₂ | — |
| 19 | 4-methylphenyl | H | —(CH₂)₃N(Et)₂ | — |
| 20 | phenyl | H | —(CH₂)₃N(Et)₂ | — |
| 21 | naphthalen-1-yl | H | —(CH₂)₃N(Et)₂ | — |
| 22 | 5-methoxy-1,3-dimethyl-1H-indol-2-yl | H | —(CH₂)₃N(Et)₂ | HI (1/1) |
| 23 | furan-3-yl | H | —(CH₂)₃N(Et)₂ | — |

The compounds of the invention were tested for their ability to bind the nicotinic receptors containing the α7 subunit using a test of binding to preparations of rat brain membranes according to the methods described hereunder:

Membrane Preparations

Frozen specimens of hippocampus from the brain of female Sprague-Dawley rats were stored at −20° C. until used. The hippocampi from 10 rats were combined and homogenized using a pulverizer of the Polytron type in 10 volumes of an ice-cooled buffer with the following composition: KCl (11 mM); KH₂PO₄ (6 mM); NaCl (137 mM); Na₂HPO₄ (8 mM); HEPES (20 mM); iodoacetamide (5 mM); EDTA (1.5 mM); PMSF (0.1 mM). The pH was adjusted to 7.4 with NaOH. The mixture obtained was centrifuged at 24000 g for 20 minutes at 4° C. and the deposit was suspended in 20 volumes of ice water. After incubating for 60 minutes at 4° C., a new deposit was obtained by centrifugation at 24000 g for 20 minutes at 4° C. This was suspended in buffer with the above composition and was frozen at −20° C. On the day of the test, the membranes were thawed, centrifuged at 24000 g for 20 minutes, then suspended at a final concentration of 2-5 mg of proteins/mL in Dulbecco phosphate buffer at pH 7.4 containing 0.05% of bovine serum albumin.

Measurement of Affinity for Receptors Containing the α7 Subunit

The binding of the compounds of the invention for receptors containing the α7 subunit was measured by competition versus [$^3$H]-methyllycaconitine ([$^3$H]-MLA), a radiolabeled tracer which recognizes the α7 receptors (Davies et al., Neuropharmacology 1999, 38, 679-690) according to conventional methods adapted to the format of 96-well plates. The ability of the compounds of the invention to displace the [$^3$H]-MLA bond on the rat hippocampus membranes was determined in duplicate after incubation for 2 hours at a temperature close to 20° C. Each well contained a sample of about 150 μg of membrane proteins, 5 nM of [$^3$H]-MLA and one of the compounds of the invention diluted to a specified concentration in Dulbecco phosphate buffer at pH 7.4 containing 0.05% of bovine serum albumin for a final volume of 150 μL. The non-specific binding was determined in specific wells containing 10 μM of non-radiolabeled MLA. Incubation was stopped by filtering the contents of each well through glass-fiber filters (Whatman GF/B) previously impregnated with a 0.33% solution of polyethylenimine in Dulbecco phosphate buffer to decrease the nonspecific binding. The filters were then washed 3 times with Dulbecco phosphate buffer, then dried at 50° C. for about 2 hours. The radioactivity retained on the filters was measured by applying scintillator (MeltiLex A, Perkin-Elmer) followed by luminometer counting (Trilux 1450 microbeta, Perkin-Elmer).

Analysis of the Results

For each compound tested, the residual radioactivity on the filters was expressed as counts per minute. The determinations in duplicate were averaged and the concentration of compound giving 50% inhibition of the specific binding of the radioactive tracer ($IC_{50}$) was calculated by curvilinear regression using special software (GraphPad Prism). The apparent affinity constants Ki of the compounds of the invention were calculated using the equation of Cheng and Prusoff (Cheng and Prusoff, Biochem. Pharmacol. 1973, 22, 3099-3108).

The compounds of the invention that were investigated in this test give a value of Ki below 10 μM. For example, compounds No. 11 and 12 showed a value of Ki of 0.737 and 0.957 μM respectively.

It therefore appears that the compounds according to the invention are ligands of nicotinic receptors containing the α7 subunit.

Thus, according to another of its aspects, the invention relates to medicinal products comprising a compound of formula (I), or a pharmaceutically acceptable salt of addition of the latter to an acid, or a hydrate or a solvate of the compound of formula (I).

These medicinal products are employed in therapeutics, notably in curative and/or symptomatic treatment, for the prevention, diagnosis and/or monitoring of the progress of disorders or diseases involving functional disturbance of the α7 nicotinic receptors or responding favorably to modulation of the latter. More particularly, the compounds of the invention can be used in psychiatric or neurological disorders or diseases of the central nervous system involving changes in cognitive functions, attention, ability to concentrate, ability to learn and remember, or the processing of sensory information. They can also be used in the treatment, prevention, diagnosis and/or monitoring of the progress of diseases involving neurodegenerative processes—either spontaneous or subsequent to lesions, acute or chronic pain and diseases involving inflammatory processes. The present invention also relates to the use, for diagnostic purposes, of analogues of these derivatives in which one or more atoms have been replaced by an isotope of atomic mass or mass number different from the atomic mass or mass number of the atoms usually occurring naturally.

The compounds of the invention can be used in the case of psychiatric or neurological disorders or diseases of the central nervous system, such as cognitive disorders, memory deficits related to age or to viral or bacterial infections, changes in ability to learn, concentrate and memorize, minor cognitive changes, senile dementias, vascular dementias, Lewy body dementia, Alzheimer's disease, Parkinson's disease, Huntington chorea, Tourette syndrome, post-traumatic neuronal degeneration, cerebrovascular accidents, cerebral ischemia or hypoxia, multisystem atrophy, progressive supranuclear paralysis, amyotrophic lateral sclerosis, peripheral neuropathies, motor disorders such as dyskinesias, tardive dyskinesias, hyperkinesias, dystonia and epilepsy, attention deficits linked to hyperactivity, schizophrenia, depression, manic-depressive psychosis, anxiety, phobias, obsessive-compulsive disorders, post-traumatic stress syndrome, panic attacks, eating disorders such as anorexia, bulimia and obesity, sleep disorders including those associated with jet-lag. The compounds of the invention can be used for establishing a reduction in the consumption of addictive substances, for helping to maintain abstinence with respect to the latter or for attenuating withdrawal symptoms. Within the scope of the present invention, the term "addictive substance" applies to legal or illegal substances whose consumption can give rise to abuse and/or dependence, such as nicotine and tobacco products, alcohol, derivatives of cannabis, opiates, cocaine, barbiturates, benzodiazepines and psychostimulants. The compounds of the invention may also be of interest in the treatment of acute or chronic pain such as postoperative pain, pain following amputation (phantom limb pain), pain associated with cancerous lesions, migraines, neuropathies and muscular pain such as fibromyalgia. Moreover, the compounds of the invention can be used in the treatment of disorders or diseases involving inflammatory processes, for example in the gastrointestinal tract: ulcerative colitis, Crohn's disease, irritable bowel syndrome, diarrhea, and elsewhere in the body arthritis (including rheumatoid arthritis) and skin inflammations such as acne. Finally, the compounds of the invention can be used in endocrine disorders such as pheochromocytoma and problems connected with smooth muscle contraction. The present invention also covers the use of the compounds of the invention for diagnostic or medical imaging purposes. It includes diagnostic and imaging methods comprising the analysis, by non-invasive methods, of the distribution of a tracer compound inside the intact body of an animal including man by physical means such as positron emission tomography, single-photon tomography, magnetic resonance spectroscopy and nuclear magnetic resonance imaging, computer-assisted X-ray tomodensitometry (scanner) or a combination of these techniques. Within the scope of the present invention, the term "tracer compound" denotes the compounds of the invention, their enantiomers or their prodrugs, used in a labeled or non-labeled form permitting them to be detected by physical means as described above. Labeling comprises replacing one or more atoms in the compounds of the invention with an isotope of atomic mass or mass number different from the atomic mass or mass number of said atoms as they usually occur naturally. It can also comprise adding, to the compounds of the invention, chemical groups bearing said isotopes, for example by means of methylating agents. The isotopes used can be, for example, isotopic radionuclides of hydrogen, carbon, nitrogen, oxygen, fluorine, phosphorus, sulfur, chlorine, iodine or technetium, such as $^2$H, $^3$H, $^{11}$C, $^{13}$C, $^{14}$C, $^{13}$N, $^{15}$O, $^{17}$O, $^{18}$F, $^{35}$S, $^{36}$Cl, $^{123}$I, $^{125}$I, $^{131}$I respectively. The labeled compounds can be synthesized by the methods described in the procedures of the present invention by substituting one or more reagents in the synthetic process with identical reagents containing the marker isotope or isotopes.

The compounds according to the invention can therefore be used for the preparation of medicinal products, in particular medicinal products intended for treatment for the prevention, diagnosis and/or monitoring of the progress of the disorders or diseases mentioned above.

According to another of its aspects, the present invention relates to pharmaceutical compositions containing, as active principle, a compound according to the invention. These pharmaceutical compositions contain an effective dose of at least one compound according to the invention, or a pharmaceutically acceptable salt, hydrate or solvate of said compound, as well as at least one pharmaceutically acceptable excipient. Said excipients are selected, according to the pharmaceutical form and the desired method of administration, from the usual excipients that are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or optionally its salt, solvate or hydrate, can be administered in a unit form of administration, mixed with conventional pharmaceutical excipients, to animals and to human beings for the prophylaxis or the treatment of the above disorders or diseases.

The suitable unit forms of administration include forms by the oral route such as tablets, soft or hard capsules, powders, granules and oral solutions or suspensions, sublingual, buccal, intratracheal, intraocular, intranasal forms of administration, administration by inhalation, topical, transdermal, subcutaneous, intramuscular or intravenous and rectal forms of administration, and implants. For topical application, the compounds according to the invention can be used in creams, gels, ointments or lotions.

As an example, a unit form of administration of a compound according to the invention in the form of a tablet can contain the following constituents:

| | |
|---|---:|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

The doses depend on the effect required, the duration of treatment and the route of administration used; they are generally between 5 mg and 1000 mg per day by the oral route for an adult with unit doses ranging from 1 mg to 250 mg of active substance.

Generally speaking, the doctor will determine the appropriate posology in relation to the age, weight and all other factors of the subject to be treated.

The present invention, according to another of its aspects, also relates to a method of treatment of the pathologies stated above, which comprises the administration, to a patient, of an effective dose of a compound according to the invention, or one of its pharmaceutically acceptable salts or hydrates or solvates.

What is claimed is:

1. A compound corresponding to formula (I):

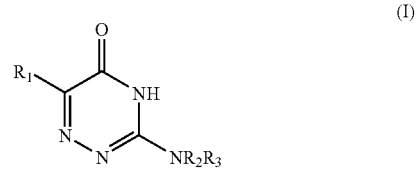

in which $R_1$ represents a heteroaryl or aryl group, said heteroaryl or aryl groups being optionally substituted by one or more groups selected from halogen, $(C_1$-$C_4)$alkyl, $(C_1$-$C_4)$alkoxy, $(C_3$-$C_7)$cycloalkyl, aryl, hydroxy, cyano, —$NH_2$ or —$NO_2$;

$R_2$ represents a hydrogen atom or a $(C_1$-$C_4)$alkyl group;

$R_3$ represents a group —$(CH_2)n$-$NR_4R_5$ in which n is equal to 2, 3 or 4; and $R_4$ and $R_5$ represent, independently of one another, a $(C_1$-$C_4)$alkyl or $(C_3$-$C_7)$cycloalkyl group, or alternatively $R_4$ and $R_5$ form together with the nitrogen atom which carries them a $(C_3$-$C_9)$heterocycloalkyl group; or a group —$(CH_2)mR_6$ in which m is equal to 0, 1, 2, 3 or 4; and $R_6$ represents a $(C_3$-$C_9)$heterocycloalkyl group containing at least one nitrogen atom and bound to the triazine ring by a carbon atom, the $(C_3$-$C_9)$heterocycloalkyl group being optionally substituted by one or more $(C_1$-$C_4)$alkyl groups;

or alternatively $R_2$ and $R_3$ form together, with the nitrogen atom which carries them, a $(C_5$-$C_9)$heterocycloalkyl containing 2 nitrogen atoms; and with the proviso that when $R_1$ represents a phenyl, $R_4$ and $R_5$ do not represent a methyl simultaneously; or said compound in the form of a salt, or a hydrate of said compound or said salt.

2. The compound of formula (I) according to claim 1, wherein $R_1$ represents a heteroaryl group, said heteroaryl group being optionally substituted by one or more groups selected from halogen, $(C_1$-$C_4)$alkyl, $(C_1$-$C_4)$alkoxy, $(C_3$-$C_7)$cycloalkyl, aryl, hydroxy, cyano, —$NH_2$ or —$NO_2$; or said compound in the form of a salt, or a hydrate of said compound or said salt.

3. The compound of formula (I) according to claim 1, wherein $R_1$ represents a heteroaryl or aryl group, said heteroaryl or aryl groups being optionally substituted by one or more groups selected from halogen, $(C_1$-$C_4)$alkyl, $(C_1$-$C_4)$alkoxy or aryl groups; or said compound in the form of a salt, or a hydrate of said compound or said salt.

4. The compound of formula (I) according to claim 1, wherein $R_1$ represents a heteroaryl group, said heteroaryl group being optionally substituted by one or more groups selected from halogen, $(C_1$-$C_4)$alkyl, $(C_1$-$C_4)$alkoxy or aryl groups; or said compound in the form of a salt, or a hydrate of said compound or said salt.

5. The compound of formula (I) according to claim 1, wherein $R_2$ represents a hydrogen atom; or said compound in the form of a salt, or a hydrate of said compound or said salt.

6. The compound of formula (I) according to claim 2, wherein $R_2$ represents a hydrogen atom; or
said compound in the form of a salt, or a hydrate of said compound or said salt.

7. The compound of formula (I) according to claim 3, wherein $R_2$ represents a hydrogen atom; or
said compound in the form of a salt, or a hydrate of said compound or said salt.

8. The compound of formula (I) according to claim 4, wherein $R_2$ represents a hydrogen atom; or
said compound in the form of a salt, or a hydrate of said compound or said salt.

9. The compound of formula (I) according to claim 5, wherein
$R_3$ represents
a group —$(CH_2)$n-$NR_4R_5$ in which
n is equal to 2, 3 or 4; and
$R_4$ and $R_5$ represent, independently of one another, a $(C_1$-$C_4)$alkyl group, or alternatively $R_4$ and $R_5$ form together, with the nitrogen atom which carries them, a $(C_3$-$C_7)$heterocycloalkyl group; or
a group —$(CH_2)$m$R_6$ in which
m is equal to 0, 1, 2, 3 or 4; and
$R_6$ represents a $(C_3$-$C_7)$heterocycloalkyl group containing at least one nitrogen atom and bound to the triazine ring by a carbon atom, the $(C_3$-$C_7)$heterocycloalkyl group being optionally substituted by one or more $(C_1$-$C_4)$alkyl groups; and
with the proviso that when $R_1$ represents a phenyl, $R_4$ and $R_5$ do not represent a methyl simultaneously; or
said compound in the form of a salt, or a hydrate of said compound or said salt.

10. The compound of formula (I) according to claim 6, wherein
$R_3$ represents
a group —$(CH_2)$n-$NR_4R_5$ in which
n is equal to 2, 3 or 4; and
$R_4$ and $R_5$ represent, independently of one another, a $(C_1$-$C_4)$alkyl group, or alternatively $R_4$ and $R_5$ form together, with the nitrogen atom which carries them, a $(C_3$-$C_7)$heterocycloalkyl group; or
a group —$(CH_2)$m$R_6$ in which
m is equal to 0, 1, 2, 3 or 4; and
$R_6$ represents a $(C_3$-$C_7)$heterocycloalkyl group containing at least one nitrogen atom and bound to the triazine ring by a carbon atom, the $(C_3$-$C_7)$heterocycloalkyl group being optionally substituted by one or more $(C_1$-$C_4)$alkyl groups; and
with the proviso that when $R_1$ represents a phenyl, $R_4$ and $R_5$ do not represent a methyl simultaneously; or
said compound in the form of a salt, or a hydrate of said compound or said salt.

11. The compound of formula (I) according to claim 7, wherein
$R_3$ represents
a group —$(CH_2)$n-$NR_4R_5$ in which
n is equal to 2, 3 or 4; and
$R_4$ and $R_5$ represent, independently of one another, a $(C_1$-$C_4)$alkyl group, or alternatively $R_4$ and $R_5$ form together, with the nitrogen atom which carries them, a $(C_3$-$C_7)$heterocycloalkyl group; or
a group —$(CH_2)$m$R_6$ in which
m is equal to 0, 1, 2, 3 or 4; and
$R_6$ represents a $(C_3$-$C_7)$heterocycloalkyl group containing at least one nitrogen atom and bound to the triazine ring by a carbon atom, the $(C_3$-$C_7)$heterocycloalkyl group being optionally substituted by one or more $(C_1$-$C_4)$alkyl groups; and
with the proviso that when $R_1$ represents a phenyl, $R_4$ and $R_5$ do not represent a methyl simultaneously; or
said compound in the form of a salt, or a hydrate of said compound or said salt.

12. The compound of formula (I) according to claim 8, wherein
$R_3$ represents
a group —$(CH_2)$n-$NR_4R_5$ in which
n is equal to 2, 3 or 4; and
$R_4$ and $R_5$ represent, independently of one another, a $(C_1$-$C_4)$alkyl group, or alternatively $R_4$ and $R_5$ form together, with the nitrogen atom which carries them, a $(C_3$-$C_7)$heterocycloalkyl group; or
a group —$(CH_2)$m$R_6$ in which
m is equal to 0, 1, 2, 3 or 4; and
$R_6$ represents a $(C_3$-$C_7)$heterocycloalkyl group containing at least one nitrogen atom and bound to the triazine ring by a carbon atom, the $(C_3$-$C_7)$heterocycloalkyl group being optionally substituted by one or more $(C_1$-$C_4)$alkyl groups; and
with the proviso that when $R_1$ represents a phenyl, $R_4$ and $R_5$ do not represent a methyl simultaneously; or
said compound in the form of a salt, or a hydrate of said compound or said salt.

13. The compound of formula (I) according to claim 1, wherein
$R_1$ represents an indolyl group, said indolyl group being optionally substituted by one or more groups selected from halogen, $(C_1$-$C_4)$alkyl, $(C_1$-$C_4)$alkoxy, $(C_3$-$C_7)$cycloalkyl, aryl, —$NH_2$ or —$NO_2$;
$R_2$ represents a hydrogen atom;
$R_3$ represents
a group —$(CH_2)$n-$NR_4R_5$ in which
n is equal to 2, 3 or 4; and
$R_4$ and $R_5$ represent, independently of one another, a $(C_1$-$C_4)$alkyl group, or alternatively $R_4$ and $R_5$ form together, with the nitrogen atom which carries them, a $(C_3$-$C_7)$heterocycloalkyl group; or
a group —$(CH_2)$m$R_6$ in which
m is equal to 0, 1, 2, 3 or 4; and
$R_6$ represents a $(C_3$-$C_7)$heterocycloalkyl group, the $(C_3$-$C_7)$heterocycloalkyl group being optionally substituted by one or more $(C_1$-$C_4)$alkyl groups; or
said compound in the form of a salt, or a hydrate of said compound or said salt.

14. A method of preparation of a compound of formula (I) according to claim 1 comprising:
reacting a compound of formula (V):

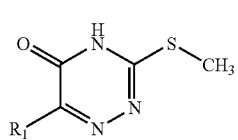

(V)

in which $R_1$ is as defined in claim 1,
with an amine of formula $HNR_2R_3$ (VI) in which $R_2$ and $R_3$ are as defined in claim 1.

15. A method of preparation of a compound of formula (I) according to claim 1 comprising:
reacting a compound of formula (VII):

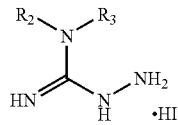

in which $R_2$ and $R_3$ are as defined in claim 1, with a compound of formula (II):

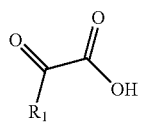

in which $R_1$ is as defined in claim 1.

16. A pharmaceutical composition comprising a compound of formula (I) or a pharmaceutically acceptable salt or a hydrate of said compound or of said salt in combination with at least one pharmaceutically acceptable excipient:

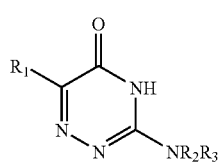

in which
$R_1$ represents a heteroaryl or aryl group, said heteroaryl or aryl groups being optionally substituted by one or more groups selected from halogen, $(C_1-C_4)$alkyl, $(C_1-C_4)$alkoxy, $(C_3-C_7)$cycloalkyl, aryl, hydroxy, cyano, —$NH_2$ or —$NO_2$;
$R_2$ represents a hydrogen atom or a $(C_1-C_4)$alkyl group;
$R_3$ represents
a group —$(CH_2)$n-$NR_4R_5$ in which
n is equal to 2, 3 or 4; and
$R_4$ and $R_5$ represent, independently of one another, a $(C_1-C_4)$alkyl or $(C_3-C_7)$cycloalkyl group, or alternatively $R_4$ and $R_5$ form together with the nitrogen atom which carries them a $(C_3-C_9)$heterocycloalkyl group; or
a group —$(CH_2)mR_6$ in which
m is equal to 0, 1, 2, 3 or 4; and
$R_6$ represents a $(C_3-C_9)$heterocycloalkyl group containing at least one nitrogen atom and bound to the triazine ring by a carbon atom, the $(C_3-C_9)$heterocycloalkyl group being optionally substituted by one or more $(C_1-C_4)$alkyl groups;
or alternatively $R_2$ and $R_3$ form together, with the nitrogen atom which carries them, a $(C_5-C_9)$heterocycloalkyl containing 2 nitrogen atoms; and
with the proviso that when $R_1$ represents a phenyl, $R_4$ and $R_5$ do not represent a methyl simultaneously.

17. The pharmaceutical composition according to claim 16, wherein
$R_1$ represents a heteroaryl group, said heteroaryl group being optionally substituted by one or more groups selected from halogen, $(C_1-C_4)$alkyl, $(C_1-C_4)$alkoxy or aryl groups; and
$R_2$ represents a hydrogen atom.

18. The pharmaceutical composition according to claim 16, wherein
$R_2$ represents a hydrogen atom;
$R_3$ represents
a group —$(CH_2)$n-$NR_4R_5$ in which
n is equal to 2, 3 or 4; and
$R_4$ and $R_5$ represent, independently of one another, a $(C_1-C_4)$alkyl group, or alternatively $R_4$ and $R_5$ form together, with the nitrogen atom which carries them, a $(C_3-C_7)$heterocycloalkyl group; or
a group —$(CH_2)mR_6$ in which
m is equal to 0, 1, 2, 3 or 4; and
$R_6$ represents a $(C_3-C_7)$heterocycloalkyl group containing at least one nitrogen atom and bound to the triazine ring by a carbon atom, the $(C_3-C_7)$heterocycloalkyl group being optionally substituted by one or more $(C_1-C_4)$alkyl groups.

19. The pharmaceutical composition according to claim 16, wherein
$R_1$ represents a heteroaryl or aryl group, said heteroaryl or aryl groups being optionally substituted by one or more groups selected from halogen, $(C_1-C_4)$alkyl, $(C_1-C_4)$alkoxy or aryl groups;
$R_2$ represents a hydrogen atom; and
$R_3$ represents
a group —$(CH_2)$n-$NR_4R_5$ in which
n is equal to 2, 3 or 4; and
$R_4$ and $R_5$ represent, independently of one another, a $(C_1-C_4)$alkyl group, or alternatively $R_4$ and $R_5$ form together, with the nitrogen atom which carries them, a $(C_3-C_7)$heterocycloalkyl group; or
a group —$(CH_2)mR_6$ in which
m is equal to 0, 1, 2, 3 or 4; and
$R_6$ represents a $(C_3-C_7)$heterocycloalkyl group containing at least one nitrogen atom and bound to the triazine ring by a carbon atom, the $(C_3-C_7)$heterocycloalkyl group being optionally substituted by one or more $(C_1-C_4)$alkyl groups.

20. The pharmaceutical composition according to claim 16, wherein
$R_1$ represents a heteroaryl or aryl group, said heteroaryl or aryl groups being optionally substituted by one or more groups selected from halogen, $(C_1-C_4)$alkyl, $(C_1-C_4)$alkoxy or aryl groups;
$R_2$ represents a hydrogen atom;
$R_3$ represents
a group —$(CH_2)$n-$NR_4R_5$ in which
n is equal to 2, 3 or 4; and
$R_4$ and $R_5$ represent, independently of one another, a $(C_1-C_4)$alkyl group, or alternatively $R_4$ and $R_5$ form together, with the nitrogen atom which carries them, a $(C_3-C_7)$heterocycloalkyl group; or
a group —$(CH_2)mR_6$ in which
m is equal to 0, 1, 2, 3 or 4; and
$R_6$ represents a $(C_3-C_7)$heterocycloalkyl group containing at least one nitrogen atom and bound to the triazine ring by a carbon atom, the $(C_3-C_7)$heterocycloalkyl group being optionally substituted by one or more $(C_1-C_4)$alkyl groups.

21. The pharmaceutical composition according to claim 16, wherein

R₁ represents a heteroaryl group, said heteroaryl 1 group being optionally substituted by one or more groups selected from halogen, $(C_1-C_4)$alkyl, $(C_1-C_4)$alkoxy or aryl groups;

R₂ represents a hydrogen atom;

R₃ represents a group —$(CH_2)n$-$NR_4R_5$ in which n is equal to 2, 3 or 4; and R₄ and R₅ represent, independently of one another, a $(C_1-C_4)$alkyl group, or alternatively R₄ and R₅ form together, with the nitrogen atom which carries them, a $(C_3-C_7)$heterocycloalkyl group; or a group —$(CH_2)mR_6$ in which m is equal to 0, 1, 2, 3 or 4; and R₆ represents a $(C_3-C_7)$heterocycloalkyl group containing at least one nitrogen atom and bound to the triazine ring by a carbon atom, the $(C_3-C_7)$heterocycloalkyl group being optionally substituted by one or more $(C_1-C_4)$ alkyl groups.

22. The pharmaceutical composition according to claim 16, wherein

R₁ represents an indolyl group, said indolyl group being optionally substituted by one or more groups selected from halogen, $(C_1-C_4)$alkyl, $(C_1-C_4$alkoxy, $(C_3-C_7)$cycloalkyl, aryl, —$NH_2$ or —$NO_2$;

R₂ represents a hydrogen atom;

R₃ represents a group —$(CH_2)n$-$NR_4R_5$ in which n is equal to 2, 3 or 4; and R₄ and R₅ represent, independently of one another, a $(C_1-C_4)$alkyl group, or alternatively R₄ and R₅ form together, with the nitrogen atom which carries them, a $(C_3-C_7)$heterocycloalkyl group; or a group —$(CH_2)mR_6$ in which m is equal to 0, 1, 2, 3 or 4; and R₆ represents a $(C_3-C_7)$heterocycloalkyl group, the $(C_3-C_7)$heterocycloalkyl group being optionally substituted by one or more $(C_1-C_4)$alkyl groups.

23. A method for the treatment of a disease in a patient, said disease selected from the group consisting of pain due to arthritis, migraine, fibromyalgia, postoperative pain, pain following amputation, pain associated with cancerous lesions, schizophrenia, Alzheimer's disease, depression and anxiety, comprising administering to said patient a therapeutically effective amount of a compound of formula (I) according to claim 1 or a pharmaceutically acceptable salt, or a hydrate of said compound or said salt.

24. The method according to claim 23, wherein the disease is pain due to arthritis, migraine, fibromyalgia, postoperative pain, pain following amputation, pain associated with cancerous lesions.

25. The method according to claim 23, wherein the disease is schizophrenia.

* * * * *